US008986669B2

(12) United States Patent
Huval et al.

(10) Patent No.: US 8,986,669 B2
(45) Date of Patent: Mar. 24, 2015

(54) METHOD FOR REMOVING PHOSPHATE AND POLYMER USED THEREFORE

(75) Inventors: Chad C. Huval, Somerville, MA (US); Stephen Randall Holmes-Farley, Arlington, MA (US); Pradeep K. Dhal, Westford, MA (US)

(73) Assignee: Genzyme Corporation, Cambridge, MA (US)

( * ) Notice: Subject to any disclaimer, the term of this patent is extended or adjusted under 35 U.S.C. 154(b) by 1581 days.

(21) Appl. No.: 11/991,209

(22) PCT Filed: Aug. 25, 2006

(86) PCT No.: PCT/US2006/033437
§ 371 (c)(1),
(2), (4) Date: May 16, 2008

(87) PCT Pub. No.: WO2007/027566
PCT Pub. Date: Mar. 8, 2007

(65) Prior Publication Data
US 2009/0047233 A1    Feb. 19, 2009

Related U.S. Application Data

(60) Provisional application No. 60/713,991, filed on Sep. 2, 2005, provisional application No. 60/734,462, filed on Nov. 8, 2005.

(51) Int. Cl.
| A61K 31/74 | (2006.01) |
| C08F 226/02 | (2006.01) |
| A61K 31/785 | (2006.01) |
| A61K 31/787 | (2006.01) |
| C08F 226/04 | (2006.01) |
| C08F 226/06 | (2006.01) |

(52) U.S. Cl.
CPC ............ *C08F 226/02* (2013.01); *A61K 31/785* (2013.01); *A61K 31/787* (2013.01); *C08F 226/04* (2013.01); *C08F 226/06* (2013.01)
USPC ..................................................... 424/78.17

(58) Field of Classification Search
None
See application file for complete search history.

(56) References Cited

U.S. PATENT DOCUMENTS

| 2,456,428 | A | 12/1948 | Parker |
| 3,104,205 | A | 9/1963 | Hainer et al. |
| 3,308,020 | A | 3/1967 | Tennant et al. |
| 3,332,841 | A | 7/1967 | Ainsworth et al. |
| 3,383,236 | A | 5/1968 | Brindamour |
| 3,431,138 | A | 3/1969 | Zingerman et al. |
| 3,539,380 | A | 11/1970 | Johnson et al. |
| 3,624,209 | A | 11/1971 | Granatek |
| 3,980,770 | A | 9/1976 | Ingelman |
| 4,071,478 | A | 1/1978 | Shen |
| 4,115,537 | A | 9/1978 | Driscoll et al. |
| 4,143,130 | A | 3/1979 | Imondi |
| 4,181,718 | A | 1/1980 | Mason et al. |
| 4,183,918 | A | 1/1980 | Asher et al. |
| 4,205,064 | A | 5/1980 | Wagner et al. |
| 4,211,763 | A | 7/1980 | Marshall et al. |
| 4,247,393 | A | 1/1981 | Wallace |
| 4,264,573 | A | 4/1981 | Powell et al. |
| 4,302,440 | A | 11/1981 | John et al. |
| 4,341,563 | A | 7/1982 | Kurihara et al. |
| 4,344,993 | A | 8/1982 | Schmidt |
| 4,504,640 | A | 3/1985 | Harada |
| 4,507,466 | A | 3/1985 | Tomalia et al. |
| 4,539,198 | A | 9/1985 | Powell et al. |
| 4,540,760 | A | 9/1985 | Harada |
| 4,543,370 | A | 9/1985 | Porter et al. |
| 4,605,701 | A | 8/1986 | Harada et al. |
| 4,631,305 | A | 12/1986 | Guyer et al. |
| 4,698,221 | A | 10/1987 | Straub |
| 4,762,524 | A | 8/1988 | Chambers et al. |
| 4,849,227 | A | 7/1989 | Cho |
| 4,871,779 | A | 10/1989 | Killat et al. |
| 4,895,621 | A | 1/1990 | Hassler |
| 4,956,182 | A | 9/1990 | Bequette et al. |
| 4,983,398 | A | 1/1991 | Gaylord et al. |
| 4,983,399 | A | 1/1991 | Maish |
| 5,053,423 | A | 10/1991 | Liu |
| 5,055,197 | A | 10/1991 | Albright et al. |
| 5,073,380 | A | 12/1991 | Babu et al. |
| 5,108,767 | A | 4/1992 | Mulchandani et al. |
| 5,194,464 | A | 3/1993 | Itoh et al. |
| 5,262,167 | A | 11/1993 | Vegesna et al. |
| 5,302,531 | A | 4/1994 | Bauer |

(Continued)

FOREIGN PATENT DOCUMENTS

| AU | 480922 | | 2/1977 |
| CH | 656 535 | A5 | 7/1986 |
| DE | 4010271 | | 2/1991 |
| EP | 0162388 | | 9/1989 |
| EP | 0379161 | | 7/1990 |
| EP | 0449151 | | 2/1991 |
| EP | 0534304 | | 3/1993 |
| EP | 0375350 | | 4/1994 |
| EP | 0605757 | | 7/1994 |
| EP | 0737759 | | 10/1996 |

(Continued)

OTHER PUBLICATIONS

Jayamurugan, Govindasamy, et al., "Synthesis of Large Generation poly(propul ether imine) (PETIM) Dendrimers" *Tetrahedron*, 62 (2006) 9582-9588.

Xiuru Li, et al., "Synthesis and Characterization of Hyperbranched Poly(ester amide)s from Commercially Available Dicarboxylic Acids and Multihydroxyl Primary Amines" *Macromolecules*, 39 (2006) 7889-7899.

(Continued)

*Primary Examiner* — Paul Dickinson
(74) *Attorney, Agent, or Firm* — Chandra Adams

(57) ABSTRACT

Polymers and compositions utilizing such polymers are disclosed for treating hyperphosphatemia and other illnesses associated with elevated serum phosphate levels. Phosphate binding polymers, or a pharmaceutically acceptable salt of the polymers, comprise pendent groups extending from a backbone of the polymer. Each pendent group comprises at least two nitrogen-bearing functional groups which bind phosphate. Variations of such polymer and compositions are disclosed.

18 Claims, No Drawings

(56) References Cited

U.S. PATENT DOCUMENTS

| | | | |
|---|---|---|---|
| 5,373,052 A | 12/1994 | Fukuda et al. |
| 5,374,422 A | 12/1994 | St. Pierre et al. |
| 5,401,515 A | 3/1995 | Woodard et al. |
| 5,414,068 A | 5/1995 | Bliem et al. |
| 5,428,112 A | 6/1995 | Ahlers et al. |
| 5,430,110 A | 7/1995 | Ahlers et al. |
| 5,447,726 A | 9/1995 | Nomura |
| 5,455,047 A | 10/1995 | Bequette et al. |
| 5,462,730 A | 10/1995 | McTaggart et al. |
| 5,487,888 A | 1/1996 | Mandeville et al. |
| 5,496,545 A | 3/1996 | Holmes-Farley et al. |
| 5,520,932 A | 5/1996 | McCurdy et al. |
| 5,530,092 A | 6/1996 | Meijer et al. |
| 5,561,214 A | 10/1996 | Yeske et al. |
| 5,607,669 A | 3/1997 | Mandeville, III et al. |
| 5,610,268 A | 3/1997 | Meijer et al. |
| 5,618,530 A | 4/1997 | Mandeville, III et al. |
| 5,624,963 A | 4/1997 | Mandeville, III et al. |
| 5,654,003 A | 8/1997 | Fuisz et al. |
| 5,667,775 A | 9/1997 | Holmes-Farley et al. |
| 5,679,717 A | 10/1997 | Mandeville, III et al. |
| 5,686,106 A | 11/1997 | Kelm et al. |
| 5,693,675 A | 12/1997 | Mandeville, III et al. |
| 5,702,696 A | 12/1997 | Mandeville, III et al. |
| 5,703,188 A | 12/1997 | Mandeville, III et al. |
| 5,709,880 A | 1/1998 | Del Corral et al. |
| 5,718,920 A | 2/1998 | Notenbomer |
| 5,747,067 A | 5/1998 | Auguello et al. |
| 5,750,148 A | 5/1998 | Maruyama et al. |
| 5,753,706 A | 5/1998 | Hsu |
| 5,807,582 A | 9/1998 | Cha |
| 5,814,336 A | 9/1998 | Kelm et al. |
| 5,840,339 A | 11/1998 | Kunin |
| 5,840,766 A | 11/1998 | Mandeville, III et al. |
| 5,900,475 A | 5/1999 | Mandeville, III et al. |
| 5,919,832 A | 7/1999 | Mandeville, III et al. |
| 5,929,184 A | 7/1999 | Holmes-Farley et al. |
| 5,959,069 A | 9/1999 | Gluck et al. |
| 5,969,090 A | 10/1999 | Mandeville, III et al. |
| 5,985,938 A | 11/1999 | Holmes-Farley et al. |
| 6,022,533 A | 2/2000 | Goto et al. |
| 6,034,129 A | 3/2000 | Mandeville, III et al. |
| 6,037,444 A | 3/2000 | Rannard et al. |
| 6,083,495 A | 7/2000 | Holmes-Farley et al. |
| 6,083,497 A | 7/2000 | Huval et al. |
| 6,090,411 A | 7/2000 | Pillay et al. |
| 6,177,478 B1 | 1/2001 | Holmes-Farley et al. |
| 6,180,094 B1 | 1/2001 | Sasaki et al. |
| 6,180,754 B1 | 1/2001 | Stutts et al. |
| 6,187,897 B1 | 2/2001 | Kawashima et al. |
| 6,190,650 B1 | 2/2001 | Matthews et al. |
| 6,203,785 B1 | 3/2001 | Holmes-Farley et al. |
| 6,248,318 B1 | 6/2001 | Huval et al. |
| 6,264,937 B1 | 7/2001 | Mandeville, III et al. |
| 6,274,713 B1 | 8/2001 | Sieving et al. |
| 6,281,252 B1 | 8/2001 | Holmes-Farley et al. |
| 6,284,275 B1 | 9/2001 | Chen |
| 6,335,402 B1 | 1/2002 | Mihan et al. |
| 6,362,266 B1 | 3/2002 | Buchholz et al. |
| 6,383,518 B1 | 5/2002 | Matsuda et al. |
| 6,410,616 B1 | 6/2002 | Harada et al. |
| 6,423,754 B1 | 7/2002 | Holmes-Farley et al. |
| 6,509,013 B1 | 1/2003 | Holmes-Farley et al. |
| 6,534,600 B2 | 3/2003 | Dvornic et al. |
| 6,566,407 B2 | 5/2003 | Holmes-Farley et al. |
| 6,600,011 B2 | 7/2003 | McDonnell et al. |
| 6,605,270 B1 | 8/2003 | Mandeville, III et al. |
| 6,696,087 B2 | 2/2004 | Matsuda et al. |
| 6,726,905 B1 | 4/2004 | Mandeville, III et al. |
| 6,733,780 B1 | 5/2004 | Tyler et al. |
| 6,844,372 B2 | 1/2005 | Goto et al. |
| 6,858,203 B2 | 2/2005 | Holmes-Farley et al. |
| 6,908,609 B2 | 6/2005 | Simon et al. |
| 6,926,912 B1 | 8/2005 | Roberts et al. |
| 7,014,846 B2 | 3/2006 | Holmes-Farley et al. |
| 7,019,085 B2 | 3/2006 | Albright |
| 7,081,509 B2 | 7/2006 | Wagner et al. |
| 7,087,223 B2 | 8/2006 | Goto et al. |
| 7,101,960 B2 | 9/2006 | Mandeville, III et al. |
| 7,220,406 B2 | 5/2007 | Burke |
| 7,229,613 B2 | 6/2007 | Burke et al. |
| 7,335,795 B2 | 2/2008 | Chang et al. |
| 7,342,083 B2 | 3/2008 | Chang et al. |
| 7,358,363 B2 | 4/2008 | Koike |
| 7,385,012 B2 | 6/2008 | Chang et al. |
| 7,449,605 B2 | 11/2008 | Chang et al. |
| 7,459,151 B2 | 12/2008 | Holmes-Farley et al. |
| 7,459,502 B2 | 12/2008 | Connor et al. |
| 7,589,238 B2 | 9/2009 | Connor et al. |
| 2002/0054903 A1 | 5/2002 | Tyler et al. |
| 2002/0114774 A1 | 8/2002 | Fitzpatrick et al. |
| 2002/0122786 A1 | 9/2002 | Matsuda et al. |
| 2002/0159968 A1 | 10/2002 | Petersen et al. |
| 2002/0160050 A1 | 10/2002 | Elema et al. |
| 2002/0168333 A1 | 11/2002 | Burke |
| 2002/0182168 A1 | 12/2002 | Holmes-Farley et al. |
| 2002/0187120 A1 | 12/2002 | Holmes-Farley et al. |
| 2002/0187121 A1 | 12/2002 | Burke |
| 2003/0039627 A1 | 2/2003 | Holmes-Farley et al. |
| 2003/0049226 A1 | 3/2003 | Burke et al. |
| 2003/0086898 A1 | 5/2003 | Holmes-Farley et al. |
| 2003/0133902 A1 | 7/2003 | Holmes-Farley et al. |
| 2003/0175349 A1 | 9/2003 | Garg et al. |
| 2003/0180250 A1 | 9/2003 | Chauhan et al. |
| 2003/0199090 A1 | 10/2003 | Monahan et al. |
| 2004/0022844 A1 | 2/2004 | Hasenzahl et al. |
| 2004/0115265 A1 | 6/2004 | Benkerrour et al. |
| 2004/0170695 A1 | 9/2004 | Elama et al. |
| 2004/0185111 A1 | 9/2004 | Rubino et al. |
| 2004/0191209 A1 | 9/2004 | Oba |
| 2004/0191212 A1 | 9/2004 | Holmes-Farley et al. |
| 2005/0084476 A1 | 4/2005 | Goto et al. |
| 2005/0096438 A1 | 5/2005 | Chang et al. |
| 2005/0123614 A1 | 6/2005 | Kim et al. |
| 2005/0131138 A1 | 6/2005 | Connor et al. |
| 2005/0131161 A1 | 6/2005 | Mandeville, III et al. |
| 2005/0147580 A1 | 7/2005 | Connor et al. |
| 2005/0165190 A1 | 7/2005 | Chang et al. |
| 2005/0208095 A1 | 9/2005 | Hunter et al. |
| 2005/0209423 A1 | 9/2005 | Chang et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0239901 A1 | 10/2005 | Chang et al. |
| 2005/0260236 A1 | 11/2005 | Tyler et al. |
| 2005/0282010 A1 | 12/2005 | Xu |
| 2006/0024336 A1 | 2/2006 | Charmot et al. |
| 2006/0029663 A1 | 2/2006 | Uchida et al. |
| 2006/0034914 A1 | 2/2006 | Tyler et al. |
| 2006/0043984 A1 | 3/2006 | Miller et al. |
| 2006/0047086 A1 | 3/2006 | Albright et al. |
| 2006/0054914 A1 | 3/2006 | Hsian Yi |
| 2006/0088592 A1 | 4/2006 | Choi et al. |
| 2006/0134225 A1 | 6/2006 | Moerck et al. |
| 2006/0171916 A1 | 8/2006 | Holmes-Farley et al. |
| 2006/0177415 A1 | 8/2006 | Burke |
| 2006/0239959 A1 | 10/2006 | Holmes-Farley et al. |
| 2006/0251614 A1 | 11/2006 | Bhagat et al. |
| 2006/0258812 A1 | 11/2006 | Gopalkrishna et al. |
| 2006/0292192 A1 | 12/2006 | Hasenzahl et al. |
| 2007/0035313 A1 | 2/2007 | Wuersch et al. |
| 2007/0059277 A1 | 3/2007 | Bhagat et al. |
| 2007/0071715 A1 | 3/2007 | DeLuca et al. |
| 2007/0094779 A1 | 5/2007 | Dauphin |
| 2007/0098678 A1 | 5/2007 | Bhagat et al. |
| 2007/0110707 A1 | 5/2007 | Ravi |
| 2007/0155950 A1 | 7/2007 | Mandeville, III et al. |
| 2007/0224283 A1 | 9/2007 | Chang et al. |

(56) References Cited

U.S. PATENT DOCUMENTS

| | | |
|---|---|---|
| 2008/0107737 A1 | 5/2008 | Chang et al. |
| 2008/0226735 A1 | 9/2008 | Moerck et al. |
| 2008/0292697 A1 | 11/2008 | Tyler et al. |

FOREIGN PATENT DOCUMENTS

| | | |
|---|---|---|
| EP | 0997148 | 5/2000 |
| EP | 1153940 | 11/2001 |
| EP | 1457256 | 9/2004 |
| EP | 1682606 | 7/2006 |
| EP | 1687349 | 8/2006 |
| EP | 1742613 | 1/2007 |
| EP | 0211991 | 3/2007 |
| EP | 1831266 | 9/2007 |
| FR | 2217010 | 9/1974 |
| FR | 2232563 | 3/1975 |
| GB | 929391 | 6/1963 |
| GB | 933108 | 8/1963 |
| GB | 1238597 | 7/1971 |
| GB | 2036048 | 6/1980 |
| GB | 1573487 | 8/1980 |
| GB | 2090605 | 7/1982 |
| GB | 2121277 | 12/1983 |
| GB | 2169356 | 7/1986 |
| GB | 2276170 | 9/1994 |
| GB | 2391730 | 2/2004 |
| JP | 5034095 | 4/1975 |
| JP | 5879022 | 5/1983 |
| JP | 60152424 | 8/1985 |
| JP | 62132830 | 6/1987 |
| JP | 4503962 | 7/1992 |
| JP | 5244915 | 9/1993 |
| JP | 6321786 | 11/1994 |
| JP | 10316576 | 12/1998 |
| JP | 2000178182 | 6/2000 |
| NL | 7401543 | 2/1974 |
| NL | 7603653 | 10/1976 |
| SU | 1808015 | 4/1993 |
| WO | WO 90/02148 | 3/1990 |
| WO | WO 92/10522 | 6/1992 |
| WO | WO 93/00915 | 1/1993 |
| WO | WO 93/05793 | 4/1993 |
| WO | WO 94/04596 | 3/1994 |
| WO | WO 94/19379 | 9/1994 |
| WO | WO 94/27620 | 12/1994 |
| WO | WO 94/27621 | 12/1994 |
| WO | WO 95/05184 | 2/1995 |
| WO | WO 95/33690 | 12/1995 |
| WO | WO 96/21454 | 7/1996 |
| WO | WO 96/25440 | 8/1996 |
| WO | WO 96/39156 | 12/1996 |
| WO | WO 97/49771 | 12/1997 |
| WO | WO 98/29107 | 7/1998 |
| WO | WO 98/42355 | 10/1998 |
| WO | WO 98/44933 | 10/1998 |
| WO | WO 99/22721 | 5/1999 |
| WO | WO 99/22743 | 5/1999 |
| WO | WO 00/22008 | 4/2000 |
| WO | WO 01/24804 | 4/2001 |
| WO | WO 01/28527 | 4/2001 |
| WO | WO 01/82871 | 11/2001 |
| WO | WO 02/062356 | 8/2002 |
| WO | WO 02/085381 A1 * | 10/2002 |
| WO | WO 03/053932 | 7/2003 |
| WO | WO 2004/037274 | 5/2004 |
| WO | WO 2004/060487 | 7/2004 |
| WO | WO 2004/099288 | 11/2004 |
| WO | WO 2005/041900 | 5/2005 |
| WO | WO 2005/041902 | 5/2005 |
| WO | WO 2005/092039 | 10/2005 |
| WO | WO 2006/043984 | 4/2006 |
| WO | WO 2006/050314 | 5/2006 |
| WO | WO 2006/061336 | 6/2006 |

OTHER PUBLICATIONS

Pérignon, Nelly et al., "Formation and Stabilization in Water of Metal Nanoparticles by a Hyperbranched Polymer Chemically Analgous to PAMAM Dendrimers" *Chem Mater.*, 16 (2004) 4856-4858.

Koç, Fikret, et al. "Highly Regioselective Synthesis pf Amino-Functionalized Dendritic PolyGlycerols by a One Pot Hydroformylation/Reductive Amination Sequence" *J. Org. Chem.*, 70 (2005) 2021-2025.

Gao, Chao, "Hyperbranched copolymers made from A2, B2 and BB'2 type monomers, 3a: comparison of copoly(sulfone-amine)s containing piperazine and 4,4'-trimethylenedipiperidine units" *Macromolecular Chemistry and Physics* (2001), 202(15), 3035-3042.

Gao, Chao, "Hyperbranched polymers made from A2- and BB2'-type monomers; 3. Polyaddition of N—methyl 1,3-propanediamine to divinyl sulfone" *Macromolecular Chemistry and Physics* (2001), 202(12), 2623-2629.

Gao, Chao, "Hyperbranched copolymers made from A2, B2 and BB'2 type monomers (iv). Copolymerization of divinyl sulfone with 4,4'-trimethylenedipiperidine and N—ethylethylenediamine" *Science in China, Series B: Chemistry* (2001), 44(2), 207-215.

Gao, C., "Preparation of Water Soluble hyperbranched poly(sulfoneamine)s by polyaddition of N—ethylethylenediamine to divinyl sulfone" *Polymer* (2001), 42(18), 7603-7610.

Gao, C., "Hyperbranched polymers made from A2, B2 and BB'2 type monomers, 2. Preparation of hyperbranched copoly(sulfone-amine)s by polyaddition of N—ethylethylenediamine and piperazine to divinylsulfone" *Polymer* (2001), 42(8), 3437-3443.

Gao, Chao, "Synthesis of hyperbranched polymers from commercially available A2 and BB'2 type monomers" *Chemical Communications* (Cambridge), 1 (2001) 107-108.

Gao, Chao, "Polyaddition of B2 and BB'2 Type Monomers to A2 Type Monomer. 1. Synthesis of Highly Branched Copoly(sulfon-amine)s" *Macromolecules* (2001), 34(2), 156-161.

Yan, Deyue, "Hyperbranched Polymers Made from A2 and BB'2 Type Monomers. 1. Polyaddition of 1-(2-Aminoethyl)piperazine to Divinyl Sulfone" *Macromolecules* (2000), 33(21), 7693-7699.

Hobson, Lois J., et al. "Poly(amidoamine) Hyperbranched Systems:Synthesis, Structure and Characterization" *Polymer*, 40 (1999) 1279-1297.

Rosenbaum, Holmes-Farley, Mandeville, Pitruzzello, Goldberg, "Effect of RenaGel, a non-absorbable, cross-linked, polymeric phosphate binder, on urinary phosphorus excretion in rats" *Nephrology Dialysis Transplantation*, vol. 12 (1997) 961-964.

Mourey, T. H., et al., "Unique Behavior of Dendritic Molecules: Intrinsic Viscosity of Polyether Dendrimers" *Macromolecules*, 25 (1992) 2401-2406.

Janssen, H.M. et al, "The Synthesis and Characterization of Dendritic Molecules" Eindhoven University of Technology [No date available].

Klapper, Marcus et al., "Poly(methylene amine): A Polymer with the Maximum Possible Number of Amino Groups on a Polymer Backbone" *Angew. Chem. Int. Ed.*, 42 (2003) 4687-4690 (XP002456407).

Kremer, Michael, et al., "Pore-Size Distributions of Cationic Polyacrylamide Hydrogels Varying in Initial Monomer Concentration and Crosslnker/Monomer Ratio" *Macromolecules*, 27 (1994) 2965-2973.

Jansen, Johan F.G.A. et al. "The Dendritic Box: Shape-Selective Liberation of Encapsulated Guests" *J. Am. Chem. Soc.*, 117 (1995) 4417-4418.

de Brabander-van den Berg, Ellen M. M. et al., "Poly(propylenimin)-Dendrimere: Synthese in größerem Maβstab durch heterogen katalysierte Hydrierungen" *Angew. Chem.* (1993) 1370-1372. [in German only].

Duncan, Ruth et al., "Dendrimer biocompatibility and toxicity" *Advanced Drug Delivery Reviews*, 57 (2005) 2215-2237.

(56) References Cited

OTHER PUBLICATIONS

Huval, Chad C. et al., "Syntheses of hydrophobically modified cationic hydrogels by copolymerization of alkyl substituted diallylamine monomers and their use as bile acid sequestrants" *European Polymer Journal*, 40 (2004) 693-701.

Newkome, George R. et al., "Improved Synthesis of an Ethereal Tetraamine Core for Dendrimer Construction" *J. Org. Chem.*, 67 (2002) 3957-3960.

Schatzlein, Andreas G. et al., "Preferential liver gene expression with polypropylenimine dendrimers" *Journal of Controlled Release*, 101 (2005) 247-258.

Shao, Lu et al., "Transport properties of cross-linked polyimide membranes induced by different generations of diaminobutane (DAB) dendrimers" *Journal of Membrane Science*, 238 (2004) 153-163.

Stasko, Nathan A. et al., "Dendrimers as a Scaffold for Nitric Oxide Release" *J. Am. Chem. Soc.*, 128 (2006) 8265-8271.

Xiao, Youchang et al., "Effects of Thermal Treatments and Dendrimers Chemical Structures on the Properties of Highly Surface Cross-Linked Polyimide Films" *Ind. Eng. Chem. Res.*, 44 (2005) 3059-3067.

Bhadra, D. et al., "Glycodendrimeric Nanoparticulate Carriers of Primaquine Phosphate for Liver Targeting" *International Journal of Pharmaceutics*, 295 (Mar. 2005) 221-233.

Pavlov, G. M. et al. "Molecular Characteristics of Poly(propylene imine) Dendrimers as Studied with Translational Diffusion and Viscometry" *Colloid. Polym. Sci.*, 280 (2002) 416-423.

Chertow, Glenn M. et al. "The Effects of Sevelamer and Calcium Acetate on Proxies of Atherosclerotic and Arteriosclerotic Vascular Disease in Hemodialysis Patients" *Am. J. Nephrol.*, 23:5 (2003) 307-314.

Katopodis, K. P. et al. "Effectiveness of Aluminum Hydroxide Timing Administration in Relation to Meals in Controlling Hyperphosphatemia in Dialysis Patients" *The International Journal of Artificial Organs*, 28:8 (2005) 803-807.

Selmeczi, B. et al. "Investigations of the Influence of Some Novel Auxiliary Agents on the Physical Properties of Tablets" *Pharmaceutical Technological Institute of the Medical University of Szeged (Hungary)*, [No date available].

Mattsson, S. et al. "Formulation of High Tensile Strength Rapidly Disintegrating Tablets Evaluation of the Effect of Some Binder Properties" *S.T.P. Pharma Sciences*, 11:3 (2001) 211-220.

Soltero, Richard et al. "The Effects of PH. Ionic Concentration and Ionic Species of Dissolution Media on the Release Rates of Quinidine Gluconate Sustained Release Dosage Forms" *Drug Development and Industrial Pharmacy*, 17:1 (1991) 113-140.

Hammouda, Y. et al. "The Use of Sodium Chloride as a Directly Compressible Filler in Therapeutic Tablets" *Pharm. Ind.*, 37:5 (1975) 361-363.

Caramella, Carla et al. "Experimental Evidence of Disintegration Mechanisms" *Acta Pharm. Technol.*, 35:1 (1989) 30-33.

Tirkkonen, Sirpa et al. "Enhancement of Drug Release from Ethylcellulose Microcapsules Using Solid Sodium Chloride in the Wall" *International Journal of Pharmaceutics*, 88 (1992) 39-51.

Mitchell, Karen et al. "The Influence of Additives on the Cloud Point, Disintegration and Dissolution of Hydroxypropylmethylcellulose Gels and Matrix Tablets" *International Journal of Pharmaceutics*, 66 (1990) 233-242.

Tirkkonen, Sirpa et al. "Release of Indomethacin from Tabletted Ethylcellulose Microcapsules" *International Journal of Pharmaceutics*, 92 (1993) 55-62.

Ferrari, F. et al. "Investigation on Bonding and Disintegration Properties of Pharmaceutical Materials" *International Journal of Pharmaceutics*, 136 (1996) 71-79.

Lin, Shan-Yang et al. "Influence of Excipients, Drugs, and Osmotic Agent in the Inner Core on the Time-Controlled Disintegration of Compression-Coated Ethylcellulose Tablets" *Journal of Pharmaceutical Sciences*, 91:9 (Sep. 2002) 2040-2046.

Schulz, W. "Brief Evaluation: Sevelamer Hydrochloride" *Drug, Therapy Criticism*, Hans Marseille Publishers GmbH, Munich, Issue 3 (2001) 621-626.

Maroni, Bradley J. et al. "Renal Bioreplacement Therapy is Associated with a Reduction in Mortality in Patients with Acute Renal Failure: Results of a Randomized, Multi-Center, Phase II Trial" *ERA-EDTA*: Abstract #551794 (2006).

"Renvela: sevelamer carbonate" Prescribing Information, Genzyme Corporation, Nov. 2007.

\* cited by examiner

METHOD FOR REMOVING PHOSPHATE AND POLYMER USED THEREFORE

RELATED APPLICATIONS

This application is the U.S. National Stage of International Application No. PCT/US2006/033437, filed Aug. 25, 2006, published in English, which under 35 U.S.C. §119 or 365 claims the benefit of U.S. Provisional Application Nos. 60/713,991, filed Sep. 2, 2005, and 60/734,462, filed Nov. 8, 2005.

The entire teachings of the above applications are incorporated herein by reference.

BACKGROUND

Hyperphosphatemia frequently accompanies diseases associated with inadequate renal function, hypoparathyroidism, and certain other medical conditions. Hyperphosphatemia is typically defined as possessing a serum phosphate level of over about 6 mg/dL. The condition, especially if present over extended periods of time, leads to severe abnormalities in calcium and phosphorus metabolism and can be manifested by aberrant calcification in joints, lungs, and eyes.

Therapeutic efforts to reduce serum phosphate include dialysis, reduction in dietary phosphate, and oral administration of insoluble phosphate binders to reduce gastrointestinal absorption. Dialysis and reduced dietary phosphate are generally unsuccessful in adequately reversing hyperphosphatemia. Further difficulties in these therapeutic regimens include the invasive nature of dialysis and the difficulties in modifying dietary habits in the latter therapy.

The oral administration of certain phosphate binders has also been suggested. Phosphate binders include calcium or aluminum salts. Calcium salts have been widely used to bind intestinal phosphate and prevent absorption. The ingested calcium combines with phosphate to form insoluble calcium phosphate salts such as $Ca_3(PO_4)_2$, $CaHPO_4$, or $Ca(H_2PO_4)_2$. Different types of calcium salts, including calcium carbonate, acetate (such as PhosLo® calcium acetate tablets), citrate, alginate, and ketoacid salts have been utilized for phosphate binding. This class of therapeutics generally results in hypercalcemia due to absorption of high amounts of ingested calcium. Hypercalcemia has been indicated in many serious side effects, such as cardiac arrhythmias, renal failure, and skin and visceral calcification. Frequent monitoring of serum calcium levels is required during therapy with calcium-based phosphate binders.

Aluminum-based phosphate binders, such as Amphojel® aluminum hydroxide gel, have also been used for treating hyperphosphatemia. These compounds complex with intestinal phosphate to form highly insoluble aluminum phosphate; the bound phosphate is unavailable for absorption by the patient. Prolonged use of aluminum gels leads to accumulations of aluminum, and often to aluminum toxicity, accompanied by such symptoms as encephalopathy, osteomalacia, and myopathy.

Selected ion exchange resins have also been suggested for use in binding phosphate. Those tested include Dowex® anion-exchange resins in the chloride form, such as XF 43311, XY 40013, XF 43254, XY 40011, and XY 40012. These resins have several drawbacks for treatment of hyperphosphatemia, including poor binding efficiency, necessitating use of high dosages for significant reduction of absorbed phosphate.

Certain anion exchange polymers, such as sevelamer hydrochloride (as disclosed in U.S. Pat. No. 5,667,775), have shown effectiveness as a phosphate sequestrant capable of lowering elevated serum phosphate levels. Sevelamer hydrochloride includes a polymer having pendent groups therefrom, the pendent groups having a single amino group. It would be desirable to develop new polymers with similar or more favorable phosphate binding properties.

SUMMARY

Disclosed herein are novel phosphate binding polymers. These polymers comprise a plurality of groups pendant from the polymer backbone. The pendant groups comprise more than one (e.g., two, three, four, or more) nitrogen-bearing functional group which binds phosphate. Some polymers disclosed herein increase the density of phosphate binding groups, and provide the groups in an arrangement to enhance phosphate binding.

One embodiment of the invention is a phosphate binding polymer or pharmaceutically acceptable salts thereof. The polymer comprises pendent groups extending from a backbone. The pendent groups comprise at least two (preferably at least three) nitrogen bearing functional groups which bind phosphate.

In a preferred embodiment of the invention, the pendent groups of the phosphate binding polymer comprise at least three nitrogen bearing functional groups. A plurality of the nitrogen bearing functional groups bind phosphate. Each pendent group is represented by Structural Formula (I):

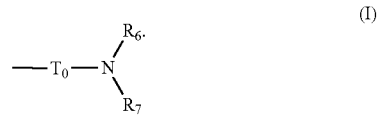

Each amine in Structural Formula (I) is independently optionally quaternarized with R.

Each group represented by R is independently hydrogen or an optionally substituted alkyl group.

$T_0$ is a covalent bond, carbonyl, Ar, Ar-$T_1$, $T_1$, O-$T_2$, S-$T_2$, C(O)-$T_1$, C(O)O-$T_2$, C(O)S-$T_1$, or C(O)N($R_T$)-$T_2$.

Ar is an optionally substituted arylene group.

$R_T$ is hydrogen or an optionally substituted C1-C3 alkyl group.

$T_1$ is an optionally substituted C1-C5 alkylene group optionally interrupted by an optionally substituted arylene group.

$T_2$ is an optionally substituted C2-C5 alkylene group.

$NR_6R_7$ taken together is a monocyclic non-aromatic ring substituted with two or more groups selected from amine, ammonium, amino alkyl, and ammonium alkyl, or a bridged bicyclic non-aromatic ring comprising at least two ring amine or ammonium groups.

Alternatively, $R_6$ is hydrogen, an optionally substituted alkyl group, or an optionally substituted aryl group, and $R_7$ is $Y_1$-Cy.

In another alternative, $R_6$ is hydrogen, an optionally substituted alkyl group, or an optionally substituted aryl group, and $R_7$ is represented by Structural Formula (Ia). In yet another alternative, $R_6$ is hydrogen, an optionally substituted alkyl group, or an optionally substituted aryl group, and $R_7$ is represented by either Structural Formula (Ia) if $T_0$ is O-$T_2$, and Structural Formula (Ib) if $T_0$ is a covalent bond, carbonyl, $T_1$, $S-T_2$, $C(O)-T_1$, $C(O)O-T_2$, $C(O)S-T_1$, or $C(O)N(R_T)-T_2$:

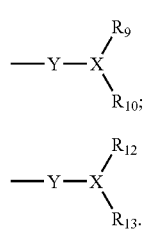

X is $C-R_X$, N or $N^+(R)$.

$R_X$ is hydrogen, an optionally substituted alkyl group, or an optionally substituted aryl group.

Y is a covalent bond or an optionally substituted C1-C10 alkylene group optionally interrupted by an optionally substituted arylene group if X is $C-R_X$; and an optionally substituted C2-C10 alkylene group optionally interrupted by an optionally substituted arylene group if X is N or $N^+(R)$.

$R_9$ is an alkyl group or an aryl group, the group substituted with at least one group selected from amine, ammonium, amino alkyl, and ammonium alkyl if X is $C-R_X$ and hydrogen, an optionally substituted allyl group, or an optionally substituted aryl group if X is N or $N^+(R)$.

$R_{10}$ is hydrogen, an optionally substituted alkyl group, or an optionally substituted aryl group. When the only value for $R_7$ is a group represented by Structural Formula (Ia) and $T_0$ is carbonyl, then $R_{10}$ is an alkyl or aryl group, the group substituted with at least one group selected from amine, ammonium, amino alkyl, and ammonium alkyl, $R_{12}$ and $R_{13}$ are each independently an alkyl group terminally substituted with amine or ammonium.

$Y_1$ is a covalent bond or an optionally substituted C1-C5 alkylene group.

Cy is a monocyclic non-aromatic ring substituted with two or more groups selected from amine, ammonium, amino alkyl, and ammonium alkyl.

Another embodiment of the present invention is a method of removing phosphate from a subject in need of such treatment. The method comprises administering to the subject an effective amount of a phosphate binding polymer disclosed herein or a pharmaceutically acceptable salt of the polymer.

Another embodiment of the invention is directed to a pharmaceutical composition comprising a pharmaceutically acceptable carrier or diluent; and a phosphate binding polymer described herein or a pharmaceutically acceptable salt of the polymer described herein. The pharmaceutical composition is used for medicinal therapy, for example, to treat a subject with hyperphosphatemia.

Yet another embodiment of the invention is the use of a disclosed phosphate binding polymer for the manufacture of a medicament for the treatment of a subject with hyperphosphatemia.

DETAILED DESCRIPTION

The disclosed phosphate binding polymers comprise multiple nitrogen-bearing functional groups that are tailored to interact with a phosphate anion. The arrangement of the nitrogen-bearing functional groups increases the density of phosphate binders and orients the binders to potentially increase binding strength and efficiency.

The disclosed phosphate binding polymers comprise pendent groups extending from the polymer backbone. Each pendent group comprises at least two nitrogen-bearing functional groups which bind phosphate. Preferably, each pendent group comprises at least three nitrogen bearing functional groups. A plurality (e.g., at least three) of the nitrogen bearing functional groups bind phosphate. Preferably, each pendent group is represented by Structural Formula (I):

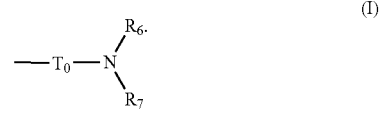

Each amine in Structural Formula (I) is independently optionally quaternarized with R.

Each group represented by R is independently hydrogen or an optionally substituted alkyl group. Suitable substituents for an allyl group represented by R are as described below for alkyl groups generally. Preferred substituents are C1-C3 alkyl group, C1-C3 haloalkyl group, hydroxy, amine, ammonium, halo, C1-C3 alkoxy or C1-C3 haloalkoxy. Preferably, R is hydrogen or an alkyl group, more preferably hydrogen.

$T_0$ is a covalent bond, carbonyl, Ar, $Ar-T_1$, $T_1$, $O-T_2$, $S-T_2$, $C(O)-T_1$, $C(O)O-T_2$, $C(O)S-T_1$, or $C(O)N(R_T)-T_2$. Preferably, $T_0$ is $O-T_2$ or $T_2$ or both. Alternatively, $T_0$ is Ar or $Ar-T_1$ or both. In another alternative, $T_0$ is a covalent bond, $Ar-T_1$, or a C1-C5 alkylene group. In yet another alternative, $T_0$ is $C(O)-T_1$. In still another alternative, $T_0$ is $O-T_2$, $S-T_2$, Ar, or $Ar-T_1$.

Ar is an optionally substituted arylene group. Preferably, Ar is an optionally substituted phenylene group, an optionally substituted pyridylene, or both. Preferred substituents for an arylene, phenylene, and pyridylene group represented by Ar include a C1-C3 alkyl group, C1-C3 haloalkyl group, hydroxy, halo, C1-C3 alkoxy or C1-C3 haloalkoxy. More preferably, Ar is a phenylene group or a pyridylene group.

$T_1$ is an optionally substituted C1-C5 alkylene group optionally interrupted by an optionally substituted arylene group, preferably an optionally substituted phenylene group. Suitable substituents for this arylene (or phenylene) group include C1-C3 alkyl group, C1-C3 haloalkyl group, hydroxy, halo, C1-C3 alkoxy or C1-C3 haloalkoxy. Suitable substituents for the alkylene group represented by $T_1$ include C1-C3 alkyl group, C1-C3 haloalkyl group, hydroxy, halo, C1-C3 alkoxy or C1-C3 haloalkoxy. Preferably, $T_1$ is $(CH_2)_j$, where j is 1, 2, 3, 4, or 5, or j is 1,2, or 3.

$T_2$ is an optionally substituted C2-C5 alkylene group. Suitable substituents for the alkylene group represented by $T_2$ include C1-C3 alkyl group, C1-C3 haloalkyl group, hydroxy, halo, C1-C3 alkoxy or C1-C3 haloalkoxy. Preferably, $T_2$ is $(CH_2)_k$, where k is 2, 3, 4, or 5, or k is 2 or 3.

$R_T$ is hydrogen or an optionally substituted C1-C3 alkyl group. Suitable substituents for an alkyl group represented by $R_T$ are as described below for alkyl groups generally. Preferred substituents are C1-C3 alkyl group, C1-C3 haloalkyl group, hydroxy, amine, ammonium, halo, C1-C3 alkoxy or C1-C3 haloalkoxy. Preferably, $R_T$ is hydrogen or a C1-C3 alkyl group.

$NR_6R_7$ taken together is a monocyclic non-aromatic ring substituted with two or more groups selected from amine, ammonium, amino alkyl, and ammonium alkyl, or a bridged bicyclic non-aromatic ring comprising at least two ring amine or ammonium groups.

Alternatively, $R_6$ is hydrogen, an optionally substituted alkyl group, or an optionally substituted aryl group, and $R_7$ is $Y_1$-Cy. Suitable substituents for the alkyl or aryl group represented by $R_6$ are described in the section below providing suitable alkyl and aryl group substituents generally. Preferred substituents are C1-C3 alkyl group, C1-C3 haloalkyl group, hydroxy, amine, ammonium, halo, C1-C3 alkoxy or C1-C3 haloalkoxy.

In another alternative, $R_6$ is hydrogen, an optionally substituted alkyl group, or an optionally substituted aryl group, and $R_7$ is represented by Structural Formula (Ia). In yet another alternative, $R_6$ is hydrogen, an optionally substituted alkyl group, or an optionally substituted aryl group, and $R_7$ is represented by either Structural Formula (Ia) if $T_0$ is O-$T_2$, and Structural Formula (Ib) if $T_0$ is a covalent bond, carbonyl, $T_1$, S-$T_2$, C(O)-$T_1$, C(O)O-$T_2$, C(O)S-$T_1$, or C(O)N($R_T$)-$T_2$:

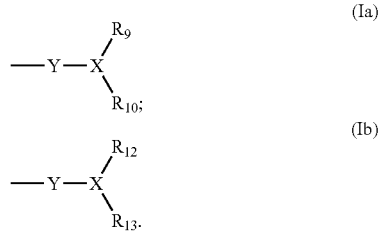

$R_9$ is hydrogen, an optionally substituted alkyl group, or an optionally substituted aryl group if X is N or $N^+(R)$; and an allyl group or an aryl group, the group substituted with at least one group selected from amine, ammonium, amino alkyl, and ammonium alkyl if X is C—$R_X$. Suitable substituents for an alkyl group and aryl group represented by $R_9$ are as described below for alkyl and aryl groups generally. Preferred substituents are C1-C3 alkyl group, C1-C3 haloalkyl group, hydroxy, amine, ammonium, halo, C1-C3 alkoxy or C1-C3 haloalkoxy. Preferably, $R_9$ is an alkyl group substituted with amine or ammonium group. More preferably, each $R_9$ is independently an alkyl group terminally substituted with amine or ammonium.

When $R_7$ is a group represented by Structural Formula (Ia) and $T_0$ is carbonyl, then $R_{10}$ is an alkyl or aryl group, the group substituted with at least one group selected from amine, ammonium, amino alkyl, and ammonium alkyl. Otherwise, $R_{10}$ is hydrogen, an optionally substituted alkyl group, or an optionally substituted aryl group. Suitable substituents for an alkyl group and aryl group represented by $R_{10}$ are as described below for alkyl and aryl groups generally. Preferred substituents are C1-C3 alkyl group, C1-C3 haloalkyl group, hydroxy, amine, ammonium, halo, C1-C3 alkoxy or C1-C3 haloalkoxy. Preferably, $R_{10}$ is hydrogen or an optionally substituted alkyl group if X is N or $N^+(R)$; and an alkyl group substituted with amine or ammonium if X is C—$R_X$. More preferably, each $R_{10}$ is independently an alkyl group terminally substituted with amine or ammonium.

$R_{12}$ and $R_{13}$ are each independently an allyl group terminally substituted with amine or ammonium.

X is C—$R_X$, N or $N^+(R)$.

$R_X$ is hydrogen, an optionally substituted alkyl group, or an optionally substituted aryl (preferably phenyl) group. Suitable substituents for the alkyl or aryl group represented by $R_X$ are provided in the section describing alkyl and aryl group substituents generally. Preferred substituents are C1-C3 alkyl group, C1-C3 haloalkyl group, hydroxy, amine, ammonium, halo, C1-C3 alkoxy or C1-C3 haloalkoxy. Preferably, $R_X$ is hydrogen, an alkyl group, or a phenyl group. More preferably, $R_X$ is hydrogen.

Y is a covalent bond or an optionally substituted C1-C10 alkylene group optionally interrupted by an optionally substituted arylene (preferably phenylene) group if X is C—$R_X$; and an optionally substituted C2-C10 alkylene group optionally interrupted by an optionally substituted arylene (preferably phenylene) group if X is N or $N^+(R)$. Suitable substituents for this arylene (or phenylene) group include C1-C3 alkyl group, C1-C3 haloalkyl group, hydroxy, halo, C1-C3 alkoxy or C1-C3 haloalkoxy. Suitable substituents for the alkylene group represented by Y include C1-C3 alkyl group, C1-C3 haloalkyl group, hydroxy, halo, C1-C3 alkoxy or C1-C3 haloalkoxy. Preferably, Y is a C1-C5 alkylene group if X is C—$R_X$ and C2-C5 allylene if X is N or $N^+(R)$.

$Y_1$ is a covalent bond or a optionally substituted C1-C5 alkylene group. Suitable substituents for the alkylene group represented by $Y_1$ include C1-C3 alkyl group, C1-C3 haloalkyl group, hydroxy, halo, C1-C3 alkoxy or C1-C3 haloalkoxy.

Cy is a monocyclic non-aromatic ring substituted with two or more groups selected from amine, ammonium, amino alkyl, and ammonium alkyl.

In a first preferred embodiment of the invention, the pendent group of the phosphate binding polymer is represented by Structural Formula (II):

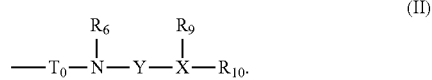

Each amine in Structural Formula (II) is independently optionally quaternarized with R. The definitions and preferred definitions for the variables of Structural Formula (II) are as described for Structural Formula (I).

Preferably for Structural Formula (II), the definitions for the variables are set forth below.

Each R is independently hydrogen or an optionally substituted alkyl group.

$R_9$ is an alkyl group substituted with amine or ammonium; and $R_{10}$ is hydrogen or an optionally substituted alkyl group when X is N or $N^+(R)$, and an alkyl group substituted with amine or ammonium when X is C—$R_X$. More preferably, $R_9$ and $R_{10}$ are each independently an alkyl group terminally substituted with amine or ammonium. The definitions and preferred definitions of the remaining variables in Structural Formula (II) are as described for Structural Formula (I).

In a second preferred embodiment of the invention, the pendent group of the disclosed phosphate binding polymer is represented by Structural Formula (IIa):

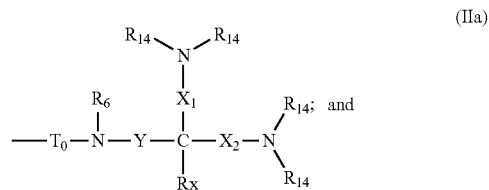

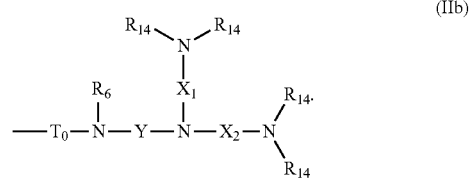

Each amine in Structural Formula (IIa) and (IIb) is independently optionally quaternarized with R.

Each R is independently hydrogen or an optionally substituted alkyl group.

Each $R_{14}$ is independently hydrogen or an optionally substituted alkyl group. Suitable substituents for an alkyl group represented by $R_{14}$ are as described below for alkyl groups generally. Preferred substituents are C1-C3 alkyl group, C1-C3 haloalkyl group, hydroxy, amine, ammonium, halo, C1-C3 alkoxy or C1-C3 haloalkoxy. Alternatively, $R_{14}$ is hydrogen.

$X_1$ and $X_2$ are each independently an optionally substituted allylene group. Suitable substituents for the alkylene group represented by $X_1$ and $X_2$ include C1-C3 alkyl group, C1-C3 haloalkyl group, hydroxy, halo, C1-C3 alkoxy or C1-C3 haloalkoxy. Alternatively for Structural Formula (IIa), $X_1$ and $X_2$ are each independently a C1-C5 alkylene group. In another alternative for Structural Formula (IIb), $X_1$ and $X_2$ are each independently a C2-C5 alkylene group. In yet another alternative, $X_1$ and $X_2$ are each $(CH_2)_j$, where j is 1, 2, 3, 4, or 5 (for Structural Formula (IIa)); or j is 2, 3, 4, or 5 (for Structural Formula (IIb)); or j is 1, 2, or 3 (for Structural Formula (IIa)); or j is 2 or 3 (for Structural Formula (IIb)).

The definitions and preferred definitions for the remaining variables in Structural Formula (IIa) and (IIb) are as described for Structural Formula (I).

More preferably in Structural Formula (IIa) and (IIb), each amine is independently optionally quaternarized with hydrogen. Even more preferably, Y is a C1-C5 allylene group for Structural Formula (IIa) and C2-C5 alkylene for Structural Formula (IIb), and $X_1$ and $X_2$ are independently C1-C5 alkylene group for Structural Formula (IIa) and C2-C5 alkylene for Structural Formula (IIb). Still more preferably, Y is a C1-C5 alkylene group for Structural Formula (IIa) and C2-C5 alkylene for Structural Formula (IIb), $X_1$ and $X_2$ are independently C1-C5 alkylene group for Structural Formula (IIa) and C2-C5 alkylene for Structural Formula (IIb), $R_X$ is hydrogen and $R_{14}$ is hydrogen.

In a third preferred embodiment of the invention, the disclosed phosphate binding polymer comprises a repeat unit represented by a structural formula selected from (IIc)-(IId):

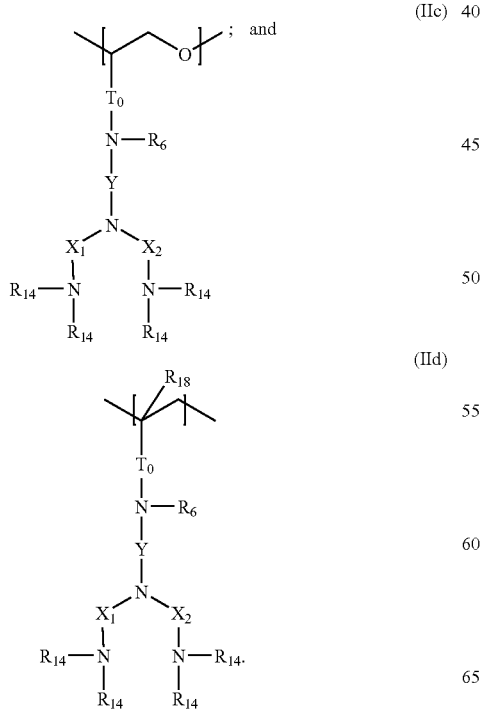

Each amine in the Structural Formulas (IIc) and (IId) above is independently optionally quaternarized with R.

Each R is independently hydrogen or an optionally substituted alkyl group.

$R_{18}$ is hydrogen or a C1-C5 alkyl group. Alternatively, $R_{18}$ is hydrogen or a methyl group. In another alternative, $R_{18}$ is a methyl group.

The definitions and preferred definitions for the variables in the structural formulas above are as described for Structural Formulas (IIa) and (IIb).

Preferably, $R_{14}$ is hydrogen and each amine of Structural Formulas (IIc) and (IId) is independently optionally quaternarized with hydrogen.

More preferably still, the disclosed phosphate binding polymer comprises a repeat unit represented by a structural formula selected from (IIe)-(IIl):

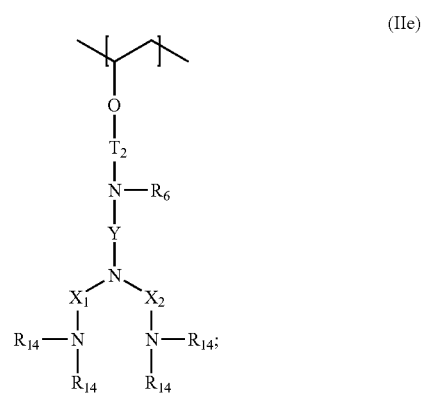

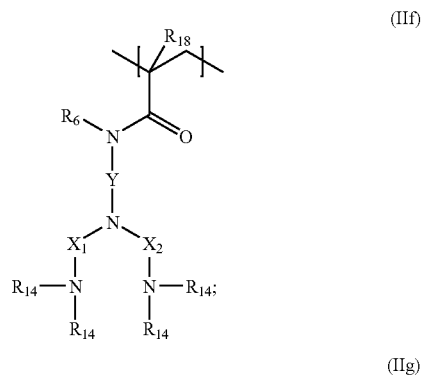

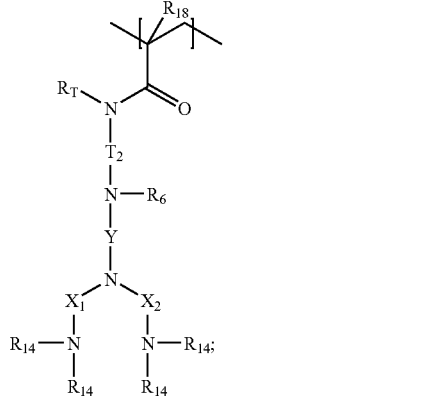

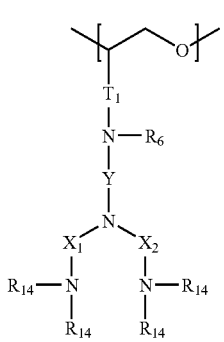 (IIh)

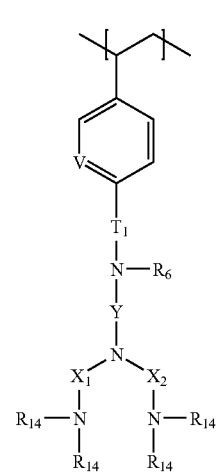 (IIi)

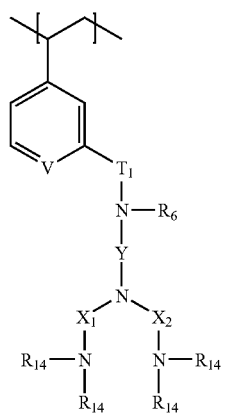 (IIj)

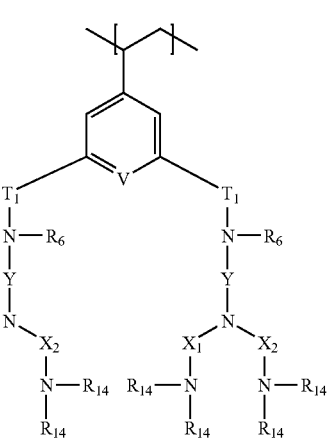 (IIk)

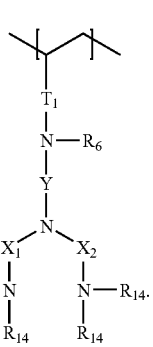 (III)

Each amine in the above structural formulas is independently optionally quaternarized with R.

Each R is independently hydrogen or an optionally substituted alkyl group.

Each V is independently N or CH.

The definitions and preferred definitions for the remaining variables in the structural formulas above are as described for Structural Formulas (IIc) and (IId) above. Preferably, $R_{14}$ is hydrogen and each amine of the above structural formulas is independently optionally quaternarized with hydrogen.

Even more preferably still, the disclosed phosphate binding polymer comprises a repeat unit represented by a structural formula selected from Structural Formulas (IIm)-(IIt):

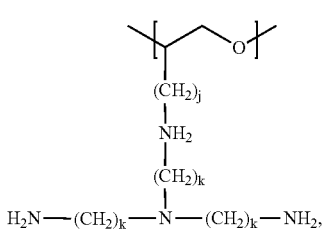 (IIm)

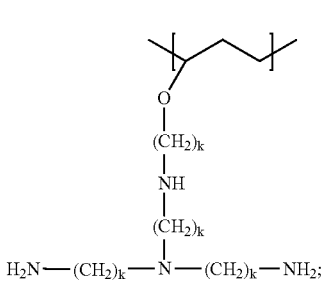 (IIn)

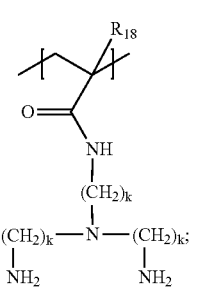 (IIo)

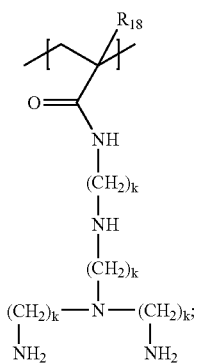
(IIp)

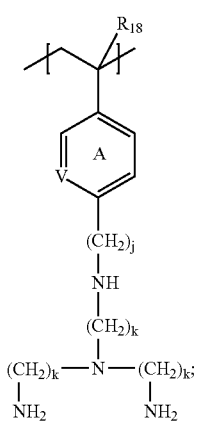
(IIq)

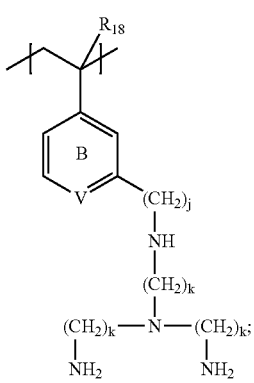
(IIr)

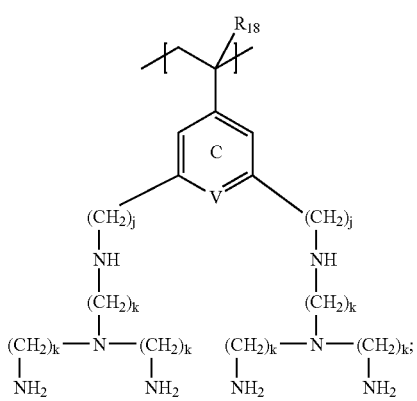
(IIs)

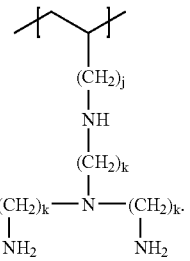
(IIt)

In Structural Formulas (IIm)-(IIt), the variables are described as follows:

$R_{18}$ is hydrogen or a methyl group.

Each V is N or CH.

Each amine is independently optionally quaternarized with hydrogen; and

Each j is independently 1, 2, 3, 4, or 5.

Each k is independently 2, 3, or 4.

Rings A-C are optionally substituted at any substitutable ring carbon atom. Each substitutent for each ring is selected indepentyl of all other substituents. Suitable substituents are as described in the section below providing suitable aryl ring substituents generally.

In a fourth preferred embodiment of the invention, the disclosed phosphate binding polymer comprises a pendent group represented by Structural Formula (III):

(III)

Each amine in Structural Formula (III) is independently optionally quaternarized with R.

Each R is independently hydrogen or an optionally substituted alkyl group.

$R_{10}$ is hydrogen or $X_3-N(R_{14})_2$ or $X_3-N^+(R_{14})_3$.

$X_3$ being an optionally substituted C1-C5 alkylene group. Suitable substituents for the alkylene group represented by $X_3$ include C1-C3 alkyl group, C1-C3 haloalkyl group, hydroxy, halo, C1-C3 alkoxy or C1-C3 haloalkoxy.

Each $R_{14}$ is independently hydrogen or an optionally substituted alkyl group. Suitable substituents for an alkyl group represented by $R_{14}$ are as described below for alkyl groups generally. Preferred substituents are C1-C3 alkyl group, C1-C3 haloalkyl group, hydroxy, amine, ammonium, halo, C1-C3 alkoxy or C1-C3 haloalkoxy. Preferably, each $R_{14}$ is independently hydrogen or an allyl group.

The remaining preferred definitions of the variables in Structural Formula (III) are as described for Structural Formula (II).

More preferably, the disclosed phosphate binding polymer comprises a pendent group represented by Structural Formula (IV):

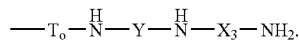
(IV)

Each amine in Structural Formula (IV) is independently optionally quaternarized with R.

Each R is independently hydrogen or an optionally substituted allyl group.

Y and $X_3$ are independently $(CH_2)_j$; j is 2, 3, or 4; and the definitions and preferred definitions of $T_0$ and the remaining variables are as described in Structural Formula (III). $T_0$ is preferably other than —C(O)N($R_7$)-$T_2$-, i.e., the pendant group represented by Structural Formula (IV) is part of polymerized monomer other than a polymerized acrylamide.

Even more preferably, the polymer comprises a repeat unit represented by a structural formula selected from:

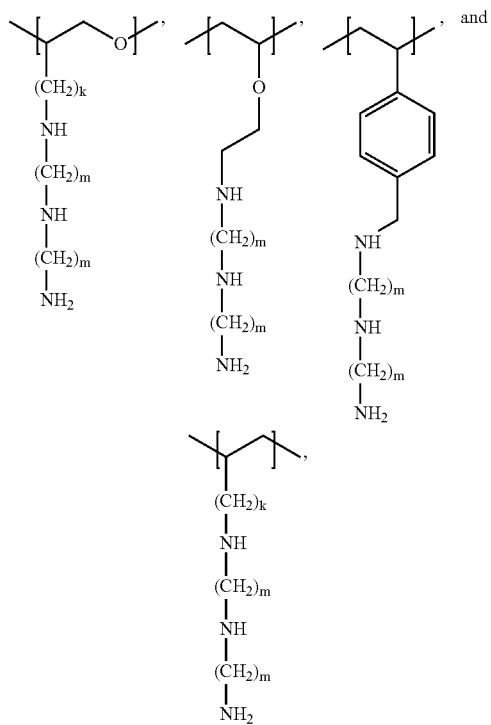

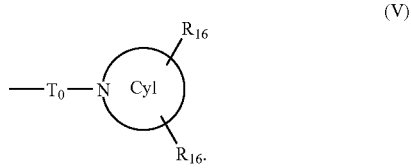

where k is 1, 2, 3, 4, or 5, and m is 2 or 3. Each amine in the structural formulas is independently optionally quaternarized with R. Each R is independently hydrogen or an optionally substituted allyl group; R is preferably hydrogen.

In a fifth preferred embodiment of the invention, the disclosed phosphate binding polymer comprises a pendent group represented by Structural Formula (V):

$$\begin{array}{c} R_{16} \\ | \\ \text{---}T_0\text{---}N\quad Cy1 \\ | \\ R_{16}. \end{array} \qquad (V)$$

Each amine of Structural Formula (V) is independently optionally quaternarized with R.

Each R is independently hydrogen or an optionally substituted alkyl group.

Cy1 is a nitrogen-containing non-aromatic ring with 3 to 7 carbon atoms.

Each $R_{16}$ is independently a C1-C3 alkyl chain terminally substituted with amine or ammonium.

$T_0$ is as described for Structural Formula (I).

More preferably, the disclosed phosphate binding polymer comprises a repeat unit represented by the one of the following structural formulas:

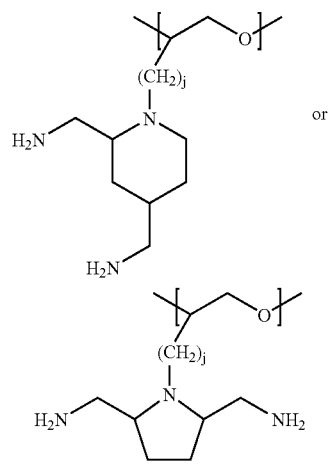

where j is 1, 2, 3, or 4. Each amine in the structural formula is optionally quaternarized with R. Each R is independently hydrogen or an optionally substituted alkyl group, preferably hydrogen or an alkyl and more preferably hydrogen.

In a sixth preferred embodiment of the invention, the disclosed phosphate binding polymer comprises a pendent group represented by Structural Formula (VI):

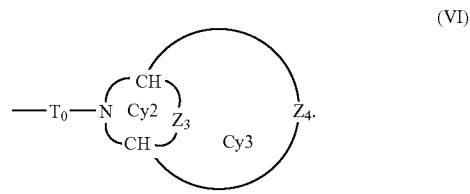

Each amine in Structural Formula (VI) is independently optionally quaternarized with R.

Each R is independently hydrogen or an optionally substituted alkyl group.

$Z_3$ and $Z_4$ are each independently an amine group or ammonium group.

Cy2 and Cy3 are each independently a 5, 6, or 7 member, non-aromatic ring with two ring nitrogen atoms.

$T_0$ is as described for Structural Formula (I).

Preferably, the disclosed phosphate binding polymer comprises a repeat unit given by the following structural formula:

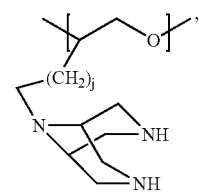

wherein each amine in the structural formula is independently optionally quaternarized with hydrogen, and j is 1, 2, 3, or 4.

In a seventh preferred embodiment of the invention, the disclosed phosphate binding polymer comprises a pendent group represented by Structural Formula (VIa):

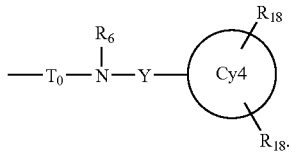

(VIa)

Each amine in Structural Formula (VIa) is independently optionally quaternarized with R.

Each R is independently hydrogen or an optionally substituted alkyl group.

Cy4 in Structural Formula (VIa) is a non-aromatic ring with 3 to 7 carbon atoms.

Each $R_{18}$ is independently a C1-C3 alkyl chain terminally substituted with amine or ammonium.

$T_0$ and $R_6$ are as described for Structural Formula (I).

Preferably, the disclosed phosphate binding polymer comprises a repeat unit represented by one of the following structural formulas:

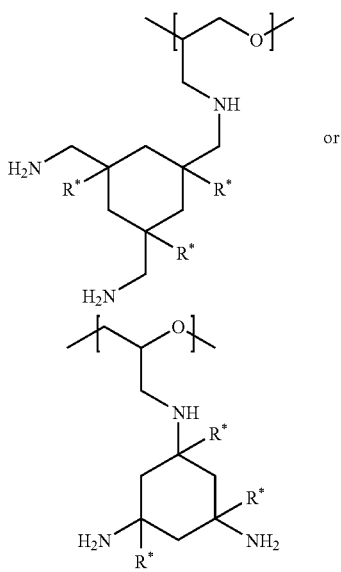

Each amine in the structural formula is independently optionally quaternarized with R; and each R and each R* is independently C1-C3 alkyl or hydrogen.

In an eighth preferred embodiment of the invention, the disclosed phosphate binding polymer is represented by one of Structural Formulas (VII) and (VIII):

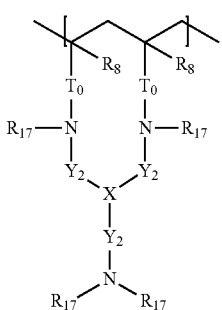

(VII)

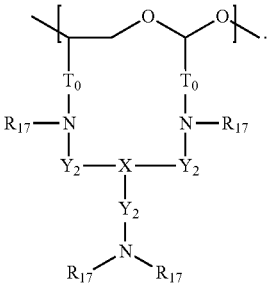

(VIII)

Each amine in Structural Formulas (VII) and (VIII) is independently optionally quaternarized with R.

Each group represented by R is independently hydrogen or an optionally substituted alkyl group. Preferably, R is hydrogen or an alkyl group, more preferably hydrogen.

$R_8$ is hydrogen or a methyl group.

Each $R_{17}$ is independently hydrogen or an optionally substituted C1-C5 alkyl group. Suitable substituents for an alkyl group represented by $R_{17}$ are as described below for alkyl groups generally. Preferred substituents are C1-C3 alkyl group, C1-C3 haloalkyl group, hydroxy, amine, ammonium, halo, C1-C3 alkoxy or C1-C3 haloalkoxy. Preferably, each $R_{17}$ is independently hydrogen or a C1-C5 alkyl group.

$T_0$ is independently a covalent bond, carbonyl, Ar, Ar-$T_1$, $T_1$, O-$T_2$, S-$T_2$, C(O)-$T_1$, C(O)O-$T_2$, C(O)S-$T_1$, or C(O)N($R_T$)-$T_2$. Preferably, $T_0$ is O-$T_2$ or $T_2$ or both. Alternatively, $T_0$ is Ar or Ar-$T_1$ or both. In another alternative, $T_0$ is a covalent bond, Ar-$T_1$, or a C1-C5 alkylene group. Preferably, each $T_0$ is the same.

$T_1$ is an optionally substituted C1-C5 alkylene group optionally interrupted by an optionally substituted arylene group, preferably an optionally substituted phenylene group. Suitable substituents for this arylene (or phenylene) group include C1-C3 alkyl group, C1-C3 haloalkyl group, hydroxy, halo, C1-C3 alkoxy or C1-C3 haloalkoxy. Suitable substituents for the alkylene group represented by $T_1$ include C1-C3 alkyl group, C1-C3 haloalkyl group, hydroxy, halo, C1-C3 alkoxy or C1-C3 haloalkoxy. Preferably, $T_1$ is $(CH_2)_j$, where j is 1, 2, 3, 4, or 5, or j is 1,2, or 3.

X is C—$R_X$, N or $N^+(R)$.

$R_X$ is hydrogen, an optionally substituted alkyl group, or an optionally substituted aryl (preferably phenyl) group. Suitable substituents for the alkyl or aryl group represented by $R_X$ are provided in the section describing alkyl and aryl group substituents generally. Preferably, $R_X$ is hydrogen, an alkyl group, or a phenyl group. More preferably, $R_X$ is hydrogen.

Each $Y_2$ is independently an optionally substituted C2-C5 alkylene when X is nitrogen, and an optionally substituted C1-C5 alkylene when X is C—$R_X$. Suitable substituents for the alkylene group represented by $Y_2$ include C1-C3 alkyl group, C1-C3 haloalkyl group, hydroxy, halo, C1-C3 alkoxy or C1-C3 haloalkoxy. In an alternative, each $Y_2$ is independently $(CH_2)_k$, where k is 1, 2, 3, 4, or 5, or k is 2, 3, 4, or 5. In another alternative, each $Y_2$ is the same.

In a ninth preferred embodiment, the pendant group of the disclosed phosphate binding polymer is represented by Structural Formulas (IX):

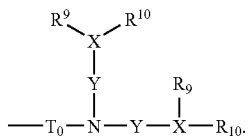

(IX)

Each amine in the pendant is optionally quaternized with hydrogen or an alkyl group. The variables in Structural Formulas (IX) are as defined in Structural Formula (II). More preferably, the phosphate binding polymer comprises a pendent group represented by Structural Formula (X):

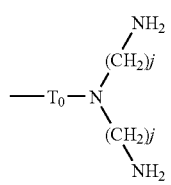

(X)

Each amine in Structural Formula (X) is independently optionally quaternarized with R.

Each R is independently hydrogen or an optionally substituted alkyl group.

Each j is independently 2 or 3.

$T_0$ is a Ar, Ar-$T_1$, O-$T_2$, S-$T_2$, C(O)-$T_1$, C(O)O-$T_2$, C(O)S-$T_1$, or C(O)N($R_T$)-$T_2$. The remainder of the variables are as defined for Structural Formula (II). The phosphate binding polymer with a pendant group represented by Structural Formulas (IX) or (X) can be, for example, polymerized styrene ($T_o$ is phenylene), polymerized vinyl alcohol ($T_o$ is O) or polymerized epichlorohydrin ($T_o$ is $CH_2$). Preferably, the polymer is a uniform co-polymer or a homopolymer.

Even more preferably, the phosphate binding polymer comprises a repeat unit represented by a structural formula selected from Structural Formulas (Xb)-(Xe):

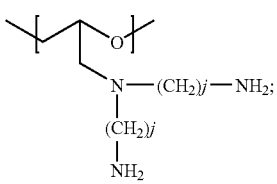

(Xb)

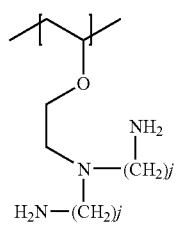

(Xc)

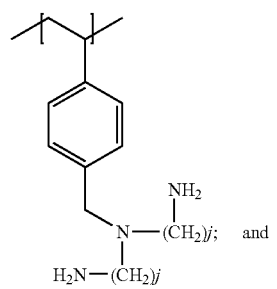

(Xd)

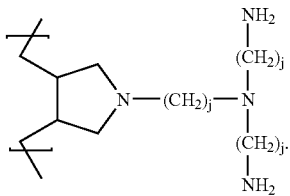

(Xe)

Each amine in Structural Formulas Xb-Xe is independently optionally quaternarized with hydrogen; and each j is independently 2 or 3.

In a tenth preferred embodiment, the phosphate binding polymer comprises a repeat unit represented by a structural formula selected from (XI)-(XIII):

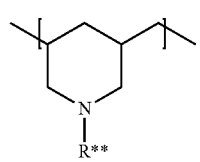

(XI)

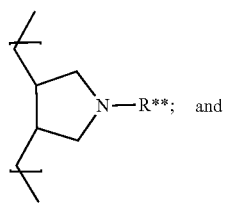

(XII)

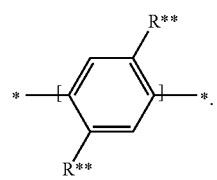

(XIII)

each R is independently represented by Structural Formula (III), (IV), (IX) or (X), provided that $T_o$ is an alkylene group for Structural Formulas (XI) and (XII) or a covalent bond or an alkylene group for Structural Formulas (XIII). Preferably, R is represented by the following structural formula:

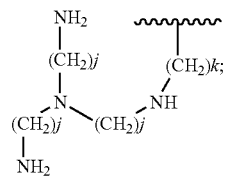

each j is independently 2 or 3;

each k is independently 1, 2, 3, 4, or 5.

and each nitrogen atom in the repeat unit is optionally quaternarized with hydrogen or an allyl group.

In another embodiment, the disclosed phosphate binding polymer comprises a repeat unit represented by Structural Formula (XIV):

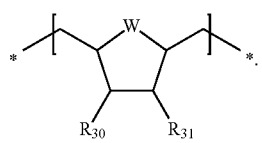

(XIV)

W is O, CH$_2$ or NH.

R$_{30}$ and R$_{31}$ are represented by Structural Formula (III), (IV), (IX) or (X), provided that T$_0$ is an alkylene group. R$_{30}$ and R$_{31}$ are independently selected.

If the disclosed phosphate binding polymer comprises a repeat unit represented by any one of Structural Formulas (A)-(G), then the polymer is a copolymer and comprises a second repeat unit. This second repeat unit comprises a multifunctional phosphate binding pendant group, which is defined below to be a pendant group which comprises at least two and preferably three nitrogen-bearing functional groups which bind phosphate. This second repeat unit is different from those represented by Structural Formulas (A)-(G). As a consequence, the multifunctional phosphate binding pendant group in this second repeat unit is not encompassed within the multifunctional phosphate binding pendant group depicted in any one of Structural Formulas (A)-(G). Polymers of this type comprise two different multifunctional phosphate binding pendant groups, one of which is encompassed within the pendant group depicted in any one of Structural Formulas (A)-(G) and the other which is not encompassed within the pendant group depicted in any one of Structural Formulas (A)-(G). More preferably, the disclosed phosphate binding polymers do not comprise a repeat unit represented by any one of Structural Formulas (A)-(G):

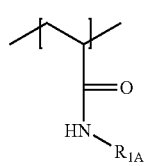

(A)

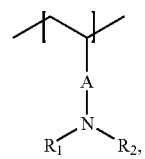

(B)

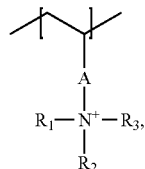

(C)

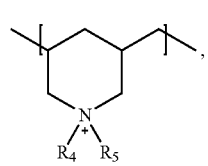

(D)

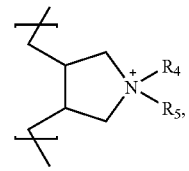

(E)

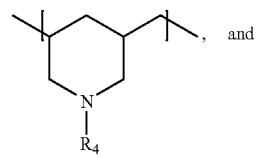

(F)

, and

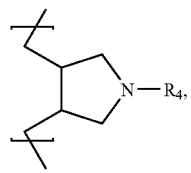

(G)

where A is either a covalent bond, CH$_2$ or C(O), R$_1$ is an alkyl amine or alkyl ammonium group, R$_{1A}$ is a polyalkyleneimine, R$_2$ and R$_3$ are each independently hydrogen, an alkyl group, an alkyl amino group, or an aryl group, R$_4$ is an alkyl ammonium group; and R$_5$ is hydrogen, or an optionally substituted alkyl group, or an optionally substituted aryl group. Alternatively, or in addition to, the disclosed phosphate binding polymer is not one of poly(tris(2-aminoethyl)amine-acrylamide) and polyepichlorohydrin/tris(2-aminoethyl)amine. In addition, the disclosed invention provides for polymers with only carbon, hydrogen and oxygen in the polymer backbone (nitrogen is not in the backbone). In addition, the polymer backbone does not comprise vicinal diaimine groups, vincinal diammonium, vicinal diaminoalkyl groups (-alkyl-amine) or vincinal diammoniumalkyl groups (-alkyl-ammonium) such as those disclosed in Chang et al., US 2005/0096438, the entire teachings of which are incorporated herein by reference. "Vincinal diamine or diammonium" refers to two amine or ammonium groups bonded to adjacent carbon atoms in the polymer backbone. "Vincinal diaminoalkyl or diammoniumalkyl" refers to two aminoalkyl or lammoniumalkyl groups on adjacent carbon atoms in the polymer.

The term "polymer" as used throughout this application refers to compounds with a molecular structure comprising repeat units or polymerized monomer units. The term "backbone" refers to that portion of the polymer which is a continuous chain, comprising the bonds which are formed between monomers upon polymerization. The composition of the polymer backbone is described without regard to the composition of branches, or side chains, off of the polymer backbone. Thus, a poly(acrylamide) polymer is said to have a polyethylene backbone, without regard to the acrylamide groups, which are components of the polymer side chains. With respect to a poly(diallylamine), the structure of which is shown below:

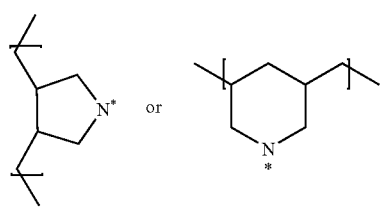

the N* atom and the carbon atoms to which it is bonded are not considered to be part of the backbone.

A "pendant group" is a group which extends from the polymer backbone. A pendent group may attach to the backbone of the polymer in one or more places (e.g., a substituted polydiallylamine). As well, a particular repeat unit of a polymer may comprise one or more pendant groups.

Phosphate binding polymers used in the present invention are selected to minimize toxicity and undesired side effects and provide effective phosphate binding. Suitable phosphate binding polymers include addition polymers such as polyolefins, for example, polystyrenes, polyallylamines, polyvinylamines, polyacrylamides orpolyacrylates. Other suitable polyolefins comprise repeat units with one of the disclosed pendant groups attached thereto. The present invention also includes condensation polymers, which are formed from reactions in which a small molecule such as water is released. Examples include a polyethers, polysulfones, polyamides, polyalkyleneimines or a polyesters. Phosphate binding polymers of the invention are commonly polyethers, which are conveniently prepared by polymerizing epichlorohydrin and then functionalizing the —$CH_2Cl$ side chain to generate a multifunctional phosphate-binding pendant group.

The disclosed phosphate binding polymers can be homopolymers and copolymers (e.g., block copolymer or random copolymer). It is understood that the term "co-polymer" means a polymer with two or more different repeat units. Typically, a co-polymer consists of two or three different repeat units, more typically two different repeat units. Thus, the disclosed phosphate binding polymers can be comprised of one distinct repeat unit, or a plurality of distinct repeat units. In addition, the polymer may be linear or branched.

The disclosed phosphate binding homopolymers and co-polymers are characterized by a pendant group which comprises at least two (preferably at least three) nitrogen-bearing functional groups which bind phosphate (hereinafter a "multifunctional phosphate-binding pendant group"). In one embodiment, every repeat unit of the disclosed phosphate binding co-polymer has a multifunctional phosphate-binding pendant group and the co-polymer comprises at least two different multifunctional phosphate-binding pendant groups. Alternatively, the disclosed phosphate binding co-polymer comprises at least one repeat unit with a multifunctional phosphate-binding pendant group and at least one repeat unit without a multifunctional phosphate-binding pendant group.

The disclosed phosphate binding co-polymers can be "mixed", meaning that the co-polymers comprise/consist of two different classes of polymerized monomers, e.g., acrylamide/acrylate, acrylamide/olefin/styrene/acrylate and the like. Alternatively, the disclosed phosphate binding co-polymers are "uniform", meaning that it consists of two different types of same class of repeat units. For example, a polyacrylamide consisting of two different polymerized acrylamide monomers would be considered uniform. "Uniform" phosphate binding co-polymers of the invention include co-polymers consisting of at least two different polymerized vinyl amines, at least two different polymerized allylamines, at least two different polymerized styrenes, at least two different polymerized acrylates, at least two different polymerized acrylamides or at least two different alkylene oxides. In one example of a "mixed" phosphate binding co-polymer, all of the repeat units comprise a multifunctional phosphate-binding group and wherein the co-polymer has at least two different types of multifunctional phosphate binding pendant group. More commonly, the disclosed phosphate binding co-polymer comprises repeat units with a multifunctional phosphate-binding pendant group and repeat units without a multifunctional phosphate binding pendant group (hereinafter "non-multifunctional pendant group"). In some instances, the non-multifunctional pendant group comprises a functional group which binds phosphate, but is not multifunctional. Examples include amine or ammonium substituted alkyl groups. Polymerized monomer units of this type include polymerized vinyl amine, polymerized allyl amine, other alkylamine substituted polymerized olefins, amino substituted polymerized styrenes, polymerized aminoalkyl acrylates, polymerized N-aminoalkyl acrylamides. Also included are the foregoing polymerized monomers wherein ammonium groups replace the amine groups. In other instances, the non-multifunctional pendant group has no group which binds phosphate to any appreciable extent. Examples include polyalkylene oxide substituted with $R^\#$, polymerized acrylates in which the ester portion is —$OR^\#$, polymerized acrylamides in which the amide portion is —$CONH_2$, —$CONHR^\#$, —$CON(R^\#)_2$, polymerized olefins substituted with $R^\#$, polymerized styrene substituted with amine, ammonium or $R^\#$, wherein $R^\#$ is alkyl optionally substituted with C1-C3 alkyl groups, halogens, hydroxyls, C1-C3 alkoxyls or C1-C3 haloalkoxyls. Example of monomers of this type include styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof. Functionalized versions of these monomers may also be used. Specific monomers or comonomers that may be used in this invention include, but are not limited to, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, 4-acryloylmorpholine, vinyl benzoic acid (all isomers), diethylaminostyrene (all isomers), α-methylvinyl benzoic acid (all isomers), diethylamino.alpha.-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylalcohol, methyl-vinylether, ethylvinylether, butylvinyltether, butadiene, isoprene, chloroprene, ethylene, vinyl acetate and combinations thereof.

In one example of a "uniform" phosphate binding co-polymer, every repeat unit of the polymer has a multifunctional phosphate-binding pendant group and the phosphate binding co-polymer comprises at least two different multifunctional nitrogen-bearing pendant groups. Alternatively, some of the repeat units comprise a multifunctional phosphate-binding pendant group and some of the repeat units do not have a multifunctional phosphate-binding pendant group. As described above, repeat units without a multifunctional phosphate-binding pendant group can have a pendant group which binds phosphate but is not multifunctional or which does not bind phosphate to any appreciable extent: Examples are as provided above.

The disclosed phosphate binding polymers are typically crosslinked. A sufficient level of crosslinring renders the polymers substantially insoluble and substantially resistant to absorption and degradation. As such, they remain substantially within the gastrointestinal tract until eliminated, thereby reducing potential side-effects in the subject.

Typically, the disclosed phosphate binding polymers are crosslinked after polymerization. One method of obtaining such crosslinking involves reaction of the polymer with difunctional crosslinkers, such as epichlorohydrin, succinyl dichloride, the diglycidyl ether of bisphenol A, pyromellitic dianhydride, toluence diisocyanate, and ethylenediamine. Examples of various polymers crosslinked with epichlorohydrin are provided herein (see Preparations 2, 4, 6, 8, 10, and 12). Crosslinking may also be achieved using other types of multi-functional crosslinking agents besides difunctional agents. Other methods of inducing crosslinking polymerized materials include, but are not limited to, exposure to ionizing radiation, ultraviolet radiation, electron beams, radicals, and pyrolysis.

Examples of preferred crosslinking agents include epichlorohydrin, 1,4 butanedioldiglycidyl ether, 1,2 ethanedioldiglycidyl ether, 1,3-dichloropropane, 1,2-dichloroethane, 1,3-dibromopropane, 1,2-dibromoethane, succinyl dichloride, dimethylsuccinate, toluene diisocyanate, acryloyl chloride, and pyromellitic dianhydride. Epichlorohydrin is a preferred crosslinking agent, because of its high availability and low cost. Epichlorohydrin is also advantageous because of its low molecular weight and hydrophilic nature, increasing the water-swellability and gel properties of the polyamine. Epichlorohydrin forms 2-hydroxypropyl crosslinking groups. In a preferred embodiment, the present invention is one of the polymers described herein crosslinked with epichlorohydrin.

Crosslinking of the disclosed phosphate binding polymers, when present, is typically between primary, secondary or tertiary amines in the pendant groups. Typically, nitrogen atoms in between 0% and 50% of the, pendent groups are bonded to a crosslinking group, preferably between 3% and 50% and more typically between 5% and 30%.

The molecular weight of polymers of the invention is not believed to be critical, provided that the molecular weight is large enough so that the polymer is not readily absorbed by the gastrointestinal tract. Typically the molecular weight is at least 1000. For example the molecular weight can be from: about 1000 to about 5 million, about 1000 to about 3 million, about 1000 to about 2 million or about 1000 to about 1 million. Crosslinked polymers, however, are not generally characterized by molecular weight.

Pharmaceutically acceptable salts of the disclosed phosphate binding polymers are encompassed within the invention. "Pharmaceutically acceptable" means suitable for pharmaceutical use. The term "salt" as used with reference to any of the polymers described herein refers to protonization of the polymer into the form of a salt. For example, some or all of the nitrogen-bearing functional groups in the polymer may be protonated to create a positively charged nitrogen atom associated with a negatively charged counterion. "Pharmaceutically acceptable salt" refers to a salt of a compound to be administered to a subject that is prepared from pharmaceutically acceptable acids including inorganic acids, organic acids, solvates, hydrates, or clathrates thereof.

Negatively charged counterions can be organic ions, inorganic ions, or a combination thereof. The inorganic ions suitable for use with embodiments of the invention include halide (especially chloride), carbonate, bicarbonate, sulfate, bisulfate, hydroxide, nitrate, persulfate and sulfite. Suitable organic ions include acetate, ascorbate, benzoate, citrate, dihydrogen citrate, hydrogen citrate, oxalate, succinate, tartrate, taurocholate, glycocholate, and cholate.

As used herein, the term "optionally quaternarized with R" indicates that one or more particularly designated amine groups may be bonded to four other groups, one of which is the "R" group, yielding the corresponding positively charged ammonium group. The "R" group is as described for Structural Formula (I). In some instances, polymers described herein comprise one or more of the structural formulas herein where each amine in the structural formula is independently optionally quaternarized with hydrogen. It is to be understood that a nitrogen atom quaternarized with R is in a "salt" form.

The term "amine" or "amine group" includes primary, secondary, and tertiary amines. The term "ammonium" or "ammonium group" refers to any amine that includes an additional substituent to the nitrogen atom, yielding a net positive charge to the group and, thus, quaternarizing the nitrogen atom.

"Nitrogen bearing functional groups which bind phosphate" include the range of functional groups containing at least one nitrogen atom that are capable of binding phosphate. Non-limiting examples include amines, ammonium, guanidines, hydrazines, imines, and amidines. Note that amides, however, are specifically excluded from the definition of a "nitrogen bearing functional group which binds phosphate" (though amides are a "nitrogen bearing functional group"). In preferred embodiments of the invention, the nitrogen bearing functional group which binds phosphate is an amine or ammonium group. A "nitrogen bearing functional group" means a functional group that comprises at least one nitrogen atom, and includes nitrogen bearing functional groups which bind phosphate and those which do not bind phosphate to any significant degree. Nitrogen bearing functional groups which do not bind phosphate include amides, carbamates and ureas.

An "alkyl group" or "alkyl", as used herein, is a saturated straight chained or branched or cyclic hydrocarbon. Typically, such groups have from one to twenty carbons, or two to twenty carbons. Preferably, the groups have from one to ten carbons, or two to ten carbons. In other instances, the groups have from one to five carbons, or two to five carbons. In another instance, the groups have one to three carbons. Suitable alkyl groups include, but are not limited to, methyl, ethyl, n-propyl, isopropyl, n-butyl, sec-butyl, tert-butyl, pentyl, isopentyl, neopentyl, hexyl, heptyl, octyl, nonyl, decyl, undecyl, dodecyl and the like. An alkyl group may be substituted with one or more substituents independently selected for each position.

The terms "aminoalkyl" refers to a straight chained or branched hydrocarbon that includes one or more amine groups. Similarly, the terms "ammoniumalkyl" and "ammonioalkyl" refer to a straight chained or branched hydrocarbon that includes one or more ammonium groups. The amine or ammonium group may interrupt an allylene or alkyl group, or may be located at an end of the group, including a terminal end of the group. The "end" of an alkyl or alkylene group refers to carbon atom at either end of the alkyl chain. The "terminal end" refers to the carbon atom of an alkyl chain which is not bonded to the remainder of the molecule. A "terminally substituted" alkyl group has a substituent at the terminal position or carbon atom.

The term "aryl group" (including aryl groups represented by $R_6$, $R_9$, $R_{10}$ and $R_X$) may be used interchangeably with "aryl," "aryl ring," "aromatic group," and "aromatic ring." Aryl groups include carbocyclic aromatic groups, typically with six to fourteen ring carbon atoms (e.g., phenyl, naphthyl, and anthracyl groups). Aryl groups also include heteroaryl groups, which typically have five to fourteen ring atoms with one or more heteroatoms selected from nitrogen, oxygen and sulfur. A heteroaryl group can be monocyclic or a fused polycyclic aromatic ring systems in which a carbocyclic aromatic ring or heteroaryl ring is fused to one or more other heteroaryl rings. Examples of heteroaryl groups include furanyl, imidazolyl, isoxazolyl, oxadiazolyl, oxazolyl, pyrazolyl, pyrrolyl, pyridyl, pyrimidinyl, pyridazinyl, thiazolyl, triazolyl, tetrazolyl, thienyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, or benzisoxazolyl. Preferably, the aryl group is a phenyl group.

An "alkylene group" (including allylene groups represented by $T_0$, $T_1$, $T_2$, $Y$, $Y_1$, $X_1$, $X_2$ and $X_3$) is represented by $-[CH_2]_z-$, wherein z is a positive integer, preferably from one to eight, more preferably from one to six. A "substituted alkylene group has one or more substituents. Suitable substituents are as described below for alkyl groups generally. Preferred substituents include C1-C3 alkyl group, C1-C3 haloalkyl group, hydroxy, halo, C1-C3 alkoxy or C1-C3 haloalkoxy.

The term "arylene" (including arylene groups represented by Ar and arylene group interrupting alkylene groups such as $T_1$ and Y) refer to an aryl ring in a molecule that are bonded to two other groups in the molecule through a single covalent bond from two of its ring atoms. Examples include phenylene $[-(C_6H_4)-]$, pyridylene $[-(C_5H_3N)-]$ and furanylene $[-(C_4H_2O)-]$. By way of example, the structure of 1,4-phenylene and 2,5-pyridylene are shown below:

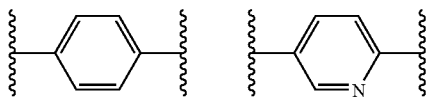 [SMILES: *c1ccc(*)cc1 ; *c1ccc(*)nc1]

Suitable substituents for an arylene are as described below for aryl groups generally. Preferred substituents include C1-C3 allyl group, C1-C3 haloalkyl group, hydroxy, halo, C1-C3 alkoxy or C1-C3 haloalkoxy. Phenylene and pyridylene are preferred arylene groups.

The term "monocyclic non-aromatic ring", refers to C3-C9 cycloalkyl groups and to monocyclic non-aromatic ring systems typically having three to nine members in which one or more ring carbons, preferably one to four, are each replaced by a heteroatom such as N, O, or S. Examples include tetrahydropyranyl, dioxanyl, tetrahydrothiophenyl, azetidinyl, oxazolidinyl, morpholinyl, thiomorpholinyl, pyrrolidinyl, piperazinyl, piperidinyl, pyrrolidinyl, thiazolidinyl and diazolonyl.

A bridged bicyclic non-aromatic ring comprises two non-aromatic rings, that share three or four adjacent ring atoms. Examples include bicyclodecyl, bicyclononyl, bicyclooctyl bicycloheptanyl bicyclohexanyl and bicyclopentyl, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl.

Optionally substituted alkyl (including alkyl groups represented by R, $R_T$, $R_6$, $R_9$, $R_{10}$, $R_{14}$, $R_X$ and $R_{17}$) or aryl groups (including aryl groups represented by $R_6$, $R_9$, $R_{10}$ and $R_X$) may carry one or more substituents which do not significantly adversely affect the phosphate binding ability of the polymers. Suitable substituents include amino, alkylamino, dialkylamino, aminocarbonyl, ammonium, dialkylammonium, trialkylammonium, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl. Preferred substituents include C1-C3 alkyl group, C1-C3 haloalkyl group, hydroxy, amino, alkylamino, dialkylamino, ammonium, dialkylammonium, trialkylammonium, halo, C1-C3 alkoxy or C1-C3 haloalkoxy.

The term polyalkyleneimine refers to $-[(CH_2)_x-NH]_yH$ wherein x is an integer from 2-10 and y is an integer from 2-20. Each x is independently selected.

Other embodiments of the invention are directed toward methods of removing phosphate from a subject in need thereof. The methods comprise administering to the subject an effective amount of a disclosed phosphate binding polymer, or a pharmaceutically acceptable salt of the polymer.

As used herein a "subject" is a mammal, preferably a human, but can also be an animal in need of veterinary treatment, such as a companion animal (e.g., dogs, cats, and the like), a farm animal (e.g., cows, sheep, pigs, horses, and the like) or a laboratory animal (e.g., rats, mice, guinea pigs, and the like).

An "effective amount" of the disclosed phosphate binding polymer is an amount that decreases the serum phosphate level of a subject suffering from a disease, ailment, or condition. Examples of such diseases, ailments, or conditions include hyperphosphatemia, inadequate renal function, hypoparathyroidism, pseudohypoparathyroidism, acute untreated acromegaly, overmedication with phosphate salts, and acute tissue destruction as occurs during-rhabdomyolysis and treatment of malignancies. Alternatively, an "effective amount" of the disclosed phosphate binding polymer is a quantity sufficient to achieve a therapeutic and/or prophylactic effect on a particular condition being treated, such as an amount which results in the prevention of or a decrease in the symptoms associated with a disease associated with hyperphosphatemia. Typical dosages of phosphate binding polymers range from about 5 milligrams/day to about 10 grams/day, preferably from about 50 milligrams/day to about 9 grams/day, more preferably from about 1 gram/day to about 8 grams/day, even more preferably about 2 grams to about 7 grams, most preferably about 4 grams/day to about 6 grams/day.

The amount of the disclosed phosphate binding polymer administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors.

The disclosed phosphate binding polymer can be administered by any suitable route, but are typically administered orally, for example, in capsules, suspensions or tablets Still other embodiments of the invention are directed toward pharmaceutical compositions comprising at least one of the disclosed phosphate binding polymers or a pharmaceutically acceptable salt of the polymer, and a diluent or pharmaceutically acceptable carrier. The phosphate binding polymers are commonly lyophilized before formulating. Optionally, one or more other therapeutic ingredients, including other phosphate binding agents, is included in such pharmaceutical compositions. The polymer may be any of the polymers described by embodiments of the invention herein.

The carriers or diluents are "acceptable" in the sense of being compatible with the other ingredients of the formulation and not deleterious to the recipient thereof. The formulations can conveniently be presented in unit dosage form and can be prepared by any suitable method known to the skilled artisan. All methods include the step of bringing into association the agent with the carrier or diluent which constitutes one or more accessory ingredients. In general, the formulations are prepared by uniformly and intimately bringing into association the phosphate binding polymer with the carriers and then, if necessary, dividing the product into unit dosages thereof.

Those skilled in the art will be aware that the amounts of the various components of the compositions of the invention to be administered in accordance with the method of the invention to a subject will depend upon those factors noted above. Such amounts may correspond with a dosage to be administered over a particular period of time to a subject (e.g., one or more tablets containing a single dose, or a sachet, slurry, food formulation, suspension, or syrup comprising a single dose).

The compositions of the invention can be formulated as a tablet, sachet, slurry, food formulation, troche, capsule, elixir, suspension, syrup, wafer, chewing gum or lozenge. A syrup formulation will generally consist of a suspension or solution of the phosphate binding polymer or salt in a liquid carrier, for example, ethanol, glycerine or water, with a flavoring or coloring agent. Where the composition is in the form of a tablet, one or more pharmaceutical carriers routinely used for preparing solid formulations can be employed. Examples of such carriers include magnesium stearate, starch, lactose and sucrose. Where the composition is in the form of a capsule, the use of routine encapsulation is generally suitable, for example, using the aforementioned carriers in a hard gelatin capsule shell Where the composition is in the form of a soft gelatin shell capsule, pharmaceutical carriers routinely used for preparing dispersions or suspensions can be considered, for example, aqueous gums, celluloses, silicates or oils, and are incorporated in a soft gelatin capsule shell.

Though the above description is directed toward routes of oral administration of pharmaceutical compositions consistent with embodiments of the invention, it is understood by those skilled in the art that any mode of administration, vehicle or carrier conventionally employed and which is inert with respect to the phosphate binding polymer may be utilized for preparing and administering the compositions. Illustrative of such methods, vehicles and carriers are those described, for example, in Remington's Pharmaceutical Sciences, 18$^{th}$ ed. (1990), the disclosure of which is incorporated herein by reference.

The phosphate binding polymers disclosed herein can be co-administered, or formulated in a pharmaceutical composition, with a pharmaceutically acceptable magnesium compound that includes a magnesium ion.

As used herein, a "pharmaceutically acceptable magnesium compound" means a compound comprising a magnesium cation, which does not cause unacceptable side effects at the dosages which are being administered. The pharmaceutically acceptable magnesium compound can be water-soluble or water-insoluble.

It is to be understood that a "pharmaceutically acceptable magnesium compound" may encompass different polymorphs of the pharmaceutically acceptable magnesium compound. The term "polymorph" refers to solid crystalline forms of a compound, which may exhibit different physical, chemical or spectroscopic properties.

The "pharmaceutically acceptable magnesium compound" may also include various solvates of the pharmaceutically acceptable magnesium compound, which include a stoichiometric or non-stoichiometric amount of solvent, e.g., water or organic solvent, bound by non-covalent intermolecular forces.

Preferred pharmaceutically acceptable magnesium compounds have a high weight percentage of magnesium, and/or have a high density. These magnesium compounds can minimize daily dose volume. Examples of magnesium compounds suitable for the invention include magnesium oxide, magnesium hydroxide, magnesium halides (e.g., magnesium fluoride, magnesium chloride, magnesium bromide and magnesium iodide), magnesium alkoxides (e.g., magnesium ethoxide and magnesium isopropoxide), magnesium carbonate, magnesium bicarbonate, magnesium formate, magnesium acetate, magnesium trisilicates, magnesium salts of organic acids, such as fumaric acid, maleic acid, acrylic acid, methacrylic acid, itaconic acid and styrenesulfonic acid, and a combination thereof. When referring to any of these magnesium compounds, it is to be understood that mixtures, polymorphs and solvates thereof are encompassed.

Examples of preferred pharmaceutically acceptable magnesium compounds in the invention include magnesium oxide, magnesium hydroxide, magnesium carbonate and magnesium formate, and a combination thereof. Other examples of preferred magnesium compounds include magnesium bicarbonate, magnesium ethoxide and magnesium trisilicate. Magnesium oxide, magnesium hydroxide, or a mixture of magnesium oxide and magnesium hydroxide is more preferred in the invention.

The phosphate binding polymers of the invention and pharmaceutically acceptable magnesium compounds can be co-formulated in a single pharmaceutical composition, or alternatively co-administered in separate pharmaceutical compositions.

When the phosphate binding polymers of the invention and pharmaceutically acceptable magnesium compounds are co-formulated in a single pharmaceutical composition, typically, the magnesium ion of the pharmaceutically acceptable magnesium compound comprises 5-35%, such as 10-30%, 10-25%, 13-25%, 15-22% and 16-20%, by anhydrous weight of the pharmaceutical composition.

Alternatively, the magnesium ion of the pharmaceutically acceptable magnesium compound comprises 5-35%, such as 10-30%, 10-25%, 13-25%, 15-22% and 16-20%, by anhydrous weight of the combined-weight of the magnesium compound and the free base of the phosphate binding polymer. Herein, the term "the free base phosphate binding polymer" means the phosphate binding polymer not including any counter ion. When the quantity of magnesium compound in the pharmaceutical composition is expressed in this fashion, it is to be understood that the phosphate binding polymer in the pharmaceutical composition can be unprotonated, partially protonated or completely protonated. However, the weight of the phosphate binding polymer is calculated assuming it is the corresponding free base phosphate binding polymer and that all of the nitrogen atoms in the phosphate binding polymer are free and not bound to any counter ions.

Alternatively, the pharmaceutically acceptable magnesium compound is present in the pharmaceutical compositions of the invention in an amount such that the molar ratio of the magnesium ion of the pharmaceutically acceptable magnesium compound to the total amine nitrogen atoms (protonated and unprotonated) of the phosphate binding polymer is 0.4-3.0, such as 0.4-2.5, 0.8-2.0, 0.8-1.5 and 0.8-1.3. Preferably, the molar ratio is 1. This ratio is the quotient of moles of magnesium ion of the pharmaceutically acceptable magnesium compound to moles of nitrogen atom in the phosphate binding polymer. If present, nitrogen from a counter ion or cross-linker is included in the moles of the phosphate binding polymer.

Alternatively, the pharmaceutically acceptable magnesium compound is present in the pharmaceutical compositions of the invention in an amount such that the weight ratio of the magnesium ion of the pharmaceutically acceptable magnesium compound to the total nitrogen atom of the phosphate binding polymer is 0.7-2.5, such as 0.7-2.0, 1.0-2.0 and 1.2-1.8. Preferably, the weight ratio is 1.57. This weight ratio is the quotient of grams of magnesium ion to grams of nitrogen atom in the phosphate binding polymer (but not the entire composition). Thus, nitrogen from a counter ion or cross-linker, if present, is included in the grams of the nitrogen atoms in the phosphate binding polymer.

Alternatively, the pharmaceutically acceptable magnesium compound is present in the pharmaceutical compositions of the invention in an amount such that the weight ratio of the magnesium ion of the pharmaceutically acceptable magnesium compound to the free base of the phosphate binding polymer is 0.2-1.2, such as 0.2-1.0, 0.3-1.0, 0.3-0.8 and 0.3-0.5. Preferably, the weight ratio is 0.42. The term "the free base of the phosphate binding polymer" is as described above. Thus, this ratio is the quotient of grams of magnesium ion to grams of phosphate binding polymer not including any weight from any counter ion in the phosphate binding polymer.

In the pharmaceutical compositions comprising a phosphate binding polymer of the invention and a pharmaceutically acceptable magnesium compound as described above, the phosphate binding polymer and pharmaceutically acceptable magnesium compound can be present in an admixture thereof. Alternatively, the pharmaceutically acceptable magnesium compound can be entrained within the phosphate binding polymer. As used herein, the term "entrained" within the phosphate binding polymer means that the phosphate binding polymer encaptures the pharmaceutically acceptable magnesium compound, for example, within a pocket (or pockets) generated by crosslinking, or by the at least two (preferably at least three) nitrogen bearing functional groups of the phosphate binding polymer.

When a pharmaceutically acceptable magnesium compound as described above is entrained within a phosphate binding polymer of the invention, preferably, the phosphate binding polymer is crosslinked. A crosslinked phosphate binding polymer entrained with a pharmaceutically acceptable magnesium compound can be prepared by crosslinking a phosphate binding polymer as described above in the presence of a pharmaceutically acceptable magnesium compound. Various examples and preferred values for the crosslinking agents are as described above. Typically, when a crosslinked phosphate binding polymer entrained with a pharmaceutically acceptable magnesium compound is employed, the crosslinking agent is present in an amount 0.5-35% (e.g., 0.5-30%, 2.5-30%, 5-25%, 5-20% or 5-15%) by weight, based upon total weight of phosphate binding polymer monomer plus crosslinking agent.

In some embodiments, the phosphate binding polymer and pharmaceutically acceptable magnesium compound are the only pharmaceutically active ingredient, e.g., the only phosphate binders, in the pharmaceutical formulations. Preferably, calcium- and aluminum-based phosphate binders are excluded from the pharmaceutical formulations. Similarly, with respect to the disclosed methods, the phosphate binding polymer and pharmaceutically acceptable magnesium compound are the only phosphate binders administered to a subject.

The disclosed phosphate binding polymers described herein may also be co-administered, or formulated in a pharmaceutical composition, with other phosphate binders including pharmaceutically acceptable lanthanum, calcium, aluminum and iron salts, such as acetates, carbonates, oxides, hydroxides, citrates, alginates, and ketoacids. Calcium salts, including calcium carbonate, acetate (such as PhosLo® calcium acetate tablets), citrate, alginate, and ketoacids, have been utilized for phosphate binding. The ingested calcium combines with phosphate to form insoluble calcium phosphate salts such as $Ca_3(PO_4)_2$, $CaHPO_4$, or $Ca(H_2PO_4)_2$. Aluminium-based phosphate binders, such as Amphojel® aluminium hydroxide gel, have also been used for treating hyperphosphatemia. These compounds complex with intestinal phosphate to form highly insoluble aluminum phosphate; the bound phosphate is unavailable for absorption by the patient. More recently iron and lanthanide salts have been used. The most commonly used lanthanide salt, lanthanum carbonate (Fosrenol®) behaves similarly to calcium carbonate. Other compositions which may be used with the phosphate binding polymers of the present invention include other types of phosphate-binding polymers (e.g., sevelamer hydrochloride as described in U.S. Pat. No. 5,667,775, which is hereby incorporated herein by reference in its entirety).

While this invention has been particularly shown and described with references to preferred embodiments thereof, it will be understood by those skilled in the art that various changes in form and details may be made therein without departing from the scope of the invention encompassed by the appended claims.

EXAMPLES

The following examples are provided to illustrate some embodiments of the invention. The examples are not intended to limit the scope of any particular embodiment utilized.

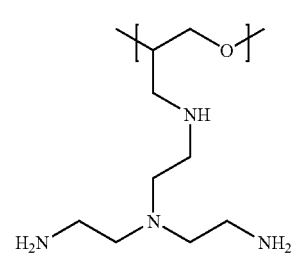

Compound 9

Compound 10
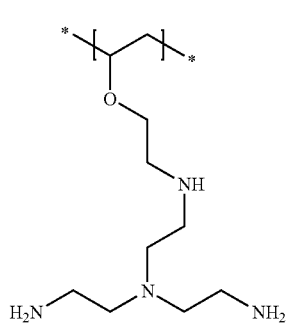
Compound 11
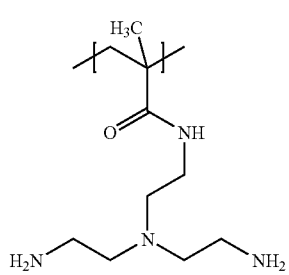
Compound 12
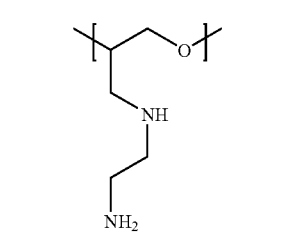
Compound 13
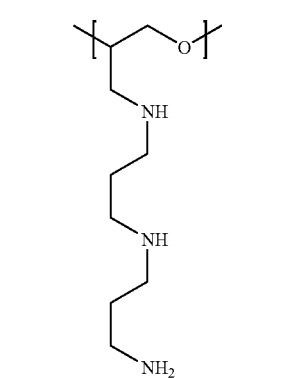
Compound 14
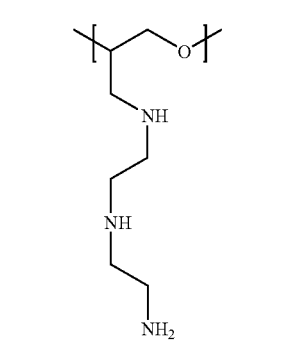
Compound 15
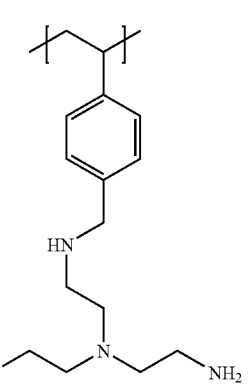
Compound 16
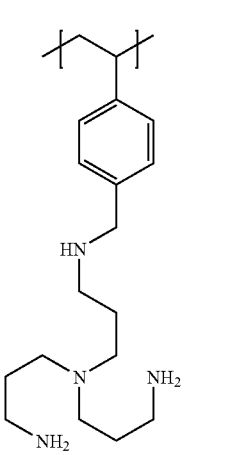
Compound 17
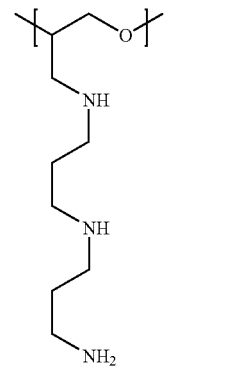
Compound 21
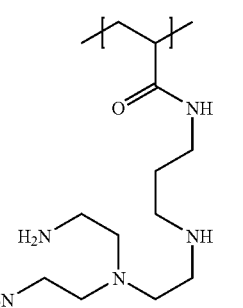

Compound 22

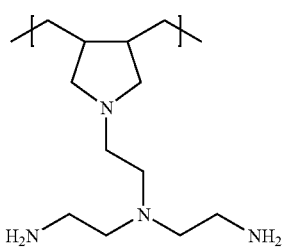

Compound 23

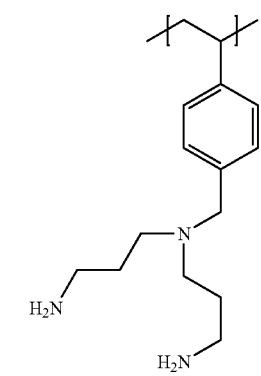

Compound 24

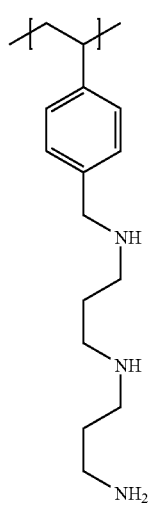

Compound 25

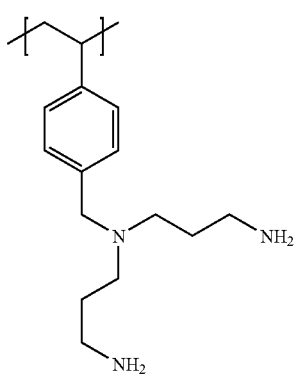

Compound 26

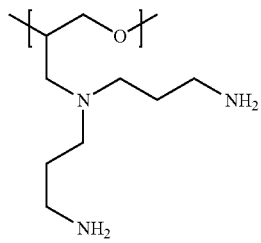

Compounds 9 through 22 were prepared and tested for phosphate binding according to the description herein.

Preparation 1

Synthesis of Poly[tris(2-aminoethy)amino)methyl oxirane] (Compound 9)

To a solution of 10.2 g of poly(epichlorohydrin) in 250 mL of 1-methyl-3pyrrolidinone was added 200 mL of tris(2-aminoethyl)amine. The reaction mixture was heated to 180° C. and was stirred at this temperature for 48 hours under nitrogen. After cooling to room temperature, the reaction mixture was poured into 2 L of diethyl ether. The precipitated polymer was filtered, dissolved in 200 mL of methanol, and was reprecipitated from 2 L of diethyl ether. The residue was collected by filtration, dried under reduced pressure, dissolved in 200 mL of deionized water, and was dialyzed against deionized water using 3500 molecular weight cut-off membrane. The dialyzed solution was lyophilized yielding 16 g of the polymer as an off white solid.

Preparation 2

Synthesis of Epichlorohydrin Crosslinked Poly[(tris(2-aminoethyl) amino)methyl oxirane] (Compound 9 crosslinked)

To a stirred solution of 11 g of Poly[tris(2-aminoethyl) amino)methyl oxirane] dissolved in 44 mL of deionized water (pH of the polymer solution=10.3) was added 390 µL of epichlorohydrin. The reaction mixture was stirred at room temperature and the solution became a gel after 60 minutes. The resulting gel was left at room temperature for 18 hours. The gel was subsequently-broken into small pieces, suspended in 600 mL of deionized water, stirred for 1 hour, and filtered. The filtered residue was suspended in 500 mL of deionized water and to this suspension concentrated HCl was added until the pH of the suspension was 7.1. After stirring for 30 minutes, the suspension was filtered. The residue was suspended in 1 L of deionized water, stirred for 40 minutes, and filtered. The residue was dried at 60° C. yielding 10.6 g of an off white solid.

Preparation 3

Synthesis of Poly{2-[tris(2-aminoethyl)aminoethyl]vinyl ether} (Compound 10)

a. Synthesis of Poly[(2-chloroethyl) vinyl ether]

To an oven-dried, 250 mL, three-necked, round bottomed flask was added 100 mL of anhydrous dichloromethane and 25 g of freshly distilled 2-chloroethylvinyl ether. The reaction mixture was stirred and bubbled with a slow stream of nitrogen for 30 minutes at room temperature. While stirring under nitrogen, it was cooled to −70° C. At −70° C., 0.5 mL of borontrifluoride diethyl etherate was added to the reaction mixture. After stirring at −70° C. for 1 hour, the reaction mixture was allowed to warm to room temperature. The reaction mixture was poured into 500 mL of MeOH and stirred for 30 minutes. The solvent was removed and the residue was redissolved in 150 mL of THF. The resulting solution was poured into 500 mL of MeOH. The solvent was removed and the precipitate was dried at 50° C. under vacuum for 24 hours, yielding 20 g of the polymer as an off-white rubbery solid.

b. Synthesis of
Poly{2-[tris(2-aminoethyl)aminoethyl]vinyl ether}

To a solution of 18 g of Poly[(2-chloroethyl) vinyl ether] dissolved in 350 mL, of 1-methyl-2-pyrrolidione was added 300 mL of tris(2-aminoethyl)amine. The reaction mixture was stirred at 180° C. under nitrogen atmosphere for 40 hours. After cooling to room temperature, the reaction mixture was poured into 3 L of diethyl ether. The suspension was stirred for 10 minutes and filtered. The residue was dissolved in 200 mL of methanol and was reprecipitated from 2 L of diethyl ether. The residue was filtered, dried, and dissolved in 200 mL of deionized water. The aqueous polymer solution was dialyzed against deionized water and the dialyzed polymer solution was lyophilized, yielding 26 g of an off white solid.

Preparation 4

Synthesis of Epichlorhydrin Crosslinked
Poly{2-[tris(2-aminoethyl) aminoethyl]vinyl ether]
(Compound 10 crosslinked)

To a stirred solution of 11.5 g of poly{2-[tris(2-aminoethyl)aminoethyl] vinyl ether} dissolved in 50 mL of deionized water (pH of the polymer solution=10.6) was added 375 µL of epichlorohydrin. The reaction mixture was stirred at room temperature and the solution became a gel after 20 minutes. The resulting gel was left at room temperature for 18 hours. The gel was subsequently broken into small pieces, suspended in 600 mL of deionized water, stirred for 1 hour, and filtered. The filtered residue was suspended in 500 mL of deionized water and to this suspension concentrated HCl was added until the pH of the suspension was 7.1. After stirring for 30 minutes, the suspension was filtered. The residue was suspended in 1 L of deionized water, stirred for 40 minutes, and filtered. The residue was dried at 60° C., yielding 10.4 g of an off white solid.

Preparation 5

Synthesis of Poly{N-{2-[bis(2-aminoethyl)ethyl]
methacrylamide} (Compound 11)

a. Synthesis of 10-Oxa-2,5,8-triazadodecanoic acid,
5-(2-aminoethyl) 11,11-dimethyl-9-oxo, 1,1-dimethylethyl ester In a 500 mL, 3-necked, round bottomed flask were taken 75 mL of anhydrous THF, 7.6 mL of tris(2-aminoethyl)amine, and 11 mL of triethylamine. The reaction mixture was cooled to −4° C. While stirring, a solution of 25 g of 2(tert-butoxy carbonyl oxyimino)-2-phenyl acetonitrile (BOC—ON reagent) dissolved in 150 mL of anhydrous THF was slowly added to the reaction mixture. The reaction mixture was slowly allowed to warm to room temperature and was stirred at room temperature for 14 hours. The reaction was diluted with 100 mL of dichloromethane and was extracted with 100 mL of brine. The organic layer was dried over anhydrous sodium sulfate, filtered, and the solvent was removed under reduced pressure. The residue was chromatographed on a silica gel column using methanol/chloroform as the mobile phase. Removal of the solvent offered 9.5 g of the product as a light yellow viscous oil.

b. Synthesis of
N-[2-[bis(2-aminoethyl)]ethyl]methacrylamide

In a 500 mL, 3-necked, round bottomed flask were taken 9.1 g of 10-oxa-2,5,8-triazadodecanoic acid, 5-(2-aminoethyl)-11,11-dimethyl-9-oxo-,1,1-dimethylethyl ester, 90 mL of anhydrous THF, and 18.6 mL of triethylamine. The solution was cooled to −5° C. While stirring, a solution of 2.6 mL of methacryloyl chloride dissolved in 10 mL of anhydrous THF was slowly added to the above reaction mixture. After addition was completed, the temperature was slowly allowed to rise to room temperature and the reaction mixture was stirred at room temperature for 16 hours. After removal of the triethylamine hydrochloride salt by filtration, the solvent was removed from the filtrate under reduced pressure. The residue was dissolved in 100 mL of dichloromethane and washed with 200 mL of deionized water. Subsequently, the organic layer was washed with 100 mL of brine. The organic layer was collected and was dried over anhydrous sodium sulfate. The solvent was removed under reduced pressure and the residue was chromatographed on a silica gel column using methanol/chloroform as the mobile phase. Removal of the solvent under reduced pressure yielded 7.4 g of a light yellow viscous oil. The oil was dissolved in 15 mL of anhydrous dioxane and was cooled to −4° C. To this cold solution was added 30 mL of 4 N HCl solution (in dioxane). The reaction mixture was allowed to warm to room temperature and was stirred for an additional two hours. A precipitate was formed, which was isolated by filtration. The residue was dried under reduced pressure yielding 5 g of the compound as an off white solid.

c. Synthesis of Poly{N-[2-[bis(2-aminoethyl)]ethyl]
methacrylamide}

To a solution of 4.8 g of N-[2-[bis(2-aminoethyl)]ethyl] methacrylamide dissolved in 6 mL of deionized water was added 26 mg of propanimidamide, 2,2'-azobis[2-methyl-, dihydrochloride (hereinafter "V-50") as the free radical polymerization initiator. The reaction mixture was flushed with a slow stream of nitrogen for 45 minutes and subsequently heated to 60° C. The reaction mixture was stirred at 60° C. for 24 hours. The solution was allowed to cool to room temperature and was dialyzed against deionized water. The dialyzed solution was lyophilized yielding 3.2 g of the polymer as an off white solid.

Preparation 6

Synthesis of Epichlorohydrin crosslinked
Poly{N-[2-[bis(2-amino
ethyl)]ethyl]methacrylamide} (Compound 11
crosslinked)

In a 50 mL round bottomed flask were taken 3 g of poly{N-[2-[bis(2-aminoethyl)]ethyl]methacrylamide} and 12 mL of deionized water. When the polymer was completely dissolved in water, the pH of the polymer solution was brought to 10.1 by using 50% aqueous NaOH solution. The polymer solution was stirred for 15 minutes and 112 mL of epichlorohydrin was added to the polymer solution. The resulting solution was stirred and gelled after 50 minutes. The reaction mixture was left at room temperature for 14 hours. The polymer gel was broken into small pieces and was stirred in 250 mL of deionized water for 45 minutes. After filtration, the gel was dispersed in 250 mL of deionized water and the pH of the solution was adjusted to 7.5 by adding concentrated HCl. The mixture was stirred for 30 minutes and filtered. The residue was dispersed in 500 mL of deionized water, stirred for 45 minutes, and filtered. The residue was dried in a forced air oven at 60° C., yielding 1.8 g of the polymer as an off white solid.

Preparation 7

Synthesis of Poly[(2-aminoethyl)amino)methyl oxirane] (Compound 12)

To a solution of 10.0 g of poly(epichlorohydrin) in 300 mL of 1-methyl-3-pyrrolidinone was added 60 mL of ethylenediamine. The reaction mixture was heated to 165° C. and was stirred at this temperature for 48 hours under nitrogen. After cooling to room temperature, the reaction mixture was poured into 4 L of diethyl ether. The precipitated polymer was filtered, dried under reduced pressure, dissolved in 200 mL of deionized water, and was dialyzed against deionized water using 3500 molecular weight cut-off membrane. The dialyzed solution was lyophilized yielding 8.3 g of the polymer as an off white solid.

Preparation 8

Synthesis of Epichlorohydrin Crosslinked Poly[(2-aminoethyl) amino)methyl oxirane] (Compound 12 crosslinked)

To a stirred solution 8.0 g of poly[(2-aminoethyl)amino) methyl oxirane] (Compound 12) dissolved in 32 mL of deionized water was added 485 µL of epichlorohydrin. The reaction mixture was stirred at room temperature and the solution became a gel after 20 minutes. The resulting gel was left at room temperature for 18 hrs. The gel was subsequently broken into small pieces, suspended in 1 L of deionized water, stirred for 1 hr, and filtered. The filtered residue was suspended in 2 L of deionized water and to this suspension concentrated HCl was added until the pH of the suspension was 7.1. After stirring for 30 minutes, the suspension was filtered. The residue was suspended in 1 L of deionized water, stirred for 40 minutes, and filtered. The residue was dried at 60° C. yielding 7.8 g of an off white solid.

Preparation 9

Synthesis of Poly[(1,3-propanediamine), N-(3-aminopropyl)N'-methyl oxirane] (Compound 13) and Compound 26

To a solution of 9.5 g of poly(epichlorohydrin) in 200 mL of 1-methyl-3-pyrrolidinone was added 100 g of N-(3-aminopropyl)1,3-propane diamine. The reaction mixture was heated to 120° C. and was stirred at this, temperature for 72 hours under nitrogen. After cooling to room temperature, the reaction mixture was poured into 2 L of diethyl ether. The precipitated polymer was filtered, washed with 1 L of diethyl ether, and dried under reduced pressure. The resulting compound was dissolved in 300 mL of deionized water, and was dialyzed against deionized water using 3500 molecular weight cut-off membrane. The dialyzed solution was lyophilized yielding 11.4 g of the polymer as an off white solid. Compound 26 is formed as a by-product.

Preparation 10

Synthesis of Epichlorohydrin Crosslinked Poly[(1,3-propanediamine), N-(3-aminopropyl)N'-methyl oxirane] (Compound 13 crosslinked)

To a stirred solution 11.0 g of poly[(1,3-propanediamine), N(3-aminopropyl)N'-methyl oxirane] (Preparation 9) dissolved in 50 mL of deionized water was added 270 µL of epichlorohydrin. The reaction mixture was stirred at room temperature and the solution became a gel after 45 minutes. The resulting gel was left at room temperature for 18 hrs. The gel was subsequently broken into small pieces, suspended in 1 L of deionized water, stirred for 1 hr, and filtered. The filtered residue was suspended in 2 L of deionized water and to this suspension concentrated HCl was added until the pH of the suspension was 7.1. After stirring for 30 minutes, the suspension was filtered. The residue was suspended in 1 L of deionized water, stirred for 40 minutes, and filtered. The residue was dried at 60° C. yielding 9 g of an off white solid.

Preparation 11

Synthesis of Poly[(1,2-ethanediamine), N-(2-aminoethyl)N'-methyl oxirane] (Compound 14)

To a solution of 9.5 g of poly(epichlorohydrin) in 200 mL of 1-methyl-3-pyrrolidinone was added 95 g of diethylenetriamine. The reaction mixture was heated to 120° C. and was stirred at this temperature for 72 hours under nitrogen. After cooling to room temperature, the reaction mixture was poured into 2 L of diethyl ether. The precipitated polymer was filtered, washed with 1 L of diethylether, and dried under reduced pressure. The resulting compound was dissolved in 300 mL of deionized water, and was dialyzed against deionized water using 3500 molecular weight cut-off membrane. The dialyzed solution was lyophilized yielding 12 g of the polymer as an off white solid.

Preparation 12

Synthesis of Epichlorohydrin Crosslinked Poly[(1,2-ethanediamine), N-(3-aminopropyl)N'-methyl oxirane] (Compound 14 crosslinked)

To a stirred solution 12.0 g of poly[(1,3-propanediamine), N(3-aminopropyl)N'-methyl oxirane] (Preparation 11) dissolved in 48 mL of deionized was added 354 µL of epichlorohydrin. The reaction mixture was stirred at room temperature and the solution became a gel after 45 minutes. The resulting gel was left at room temperature for 18 hrs. The gel was subsequently broken into small pieces, suspended in 0.1 L of deionized water, stirred for 1 hr, and filtered. The filtered residue was suspended in 2 L of deionized water and to this suspension concentrated HCl was added until the pH of the suspension was 7.1. After stirring for 30 minutes, the suspension was filtered. The residue was suspended in 1 L of deionized water, stirred for 40 minutes, and filtered. The residue was dried at 60° C. yielding 10 g of an off white solid.

Preparation 13

Synthesis of Poly [4-{(tris(2-aminoethyl)amino) methyl}styrene] (Compound 15).

The synthesis of this polymer involves two steps: synthesis of the monomer and its subsequent free radical polymerization.

13a. Synthesis of 4-{(tris(2-aminoethyl)amino) methyl}styrene.

In a 500 mL, 3-necked round-bottomed flask were taken 191.5 g of tris(2-aminoethyl)amine and 48.16 g of anhydrous potassium carbonate. To this suspension was added a solution of 44.2 g of 4-vinylbenzyl chloride in 30 mL of chloroform. The resulting reaction mixture was stirred at 25° C. for 18 hr. Subsequently the reaction mixture was filtered. The filtrate was extracted with borate buffer of pH 9.5 (2×400 mL). The aqueous extracts were combined and the pH of this aqueous solution was brought to 12.5 by using 40% (w/w) aqueous sodium hydroxide solution. The resulting solution was extracted with chloroform (3×1 L). The combined organic phase was dried over anhydrous potassium carbonate, filtered, and the solvent was removed under reduced pressure yielding 25.6 of the product as a light yellow oil.

13b. Polymerization of 4-{(tris(2-aminoethyl)amino)methyl}styrene.

A 500 mL, 3-necked round-bottomed flask was charged with 25.15 g of {(tris(2-aminoethyl)amino) methyl}styrene (example 13a) and 226 ml of deionized water. To this solution, 37% aqueous HCl was added slowly (by maintaining the temperature to below 15° C. by using an ice-bath) until the pH of the solution was 1.4. This was followed by the addition of 250 mg of V-50. While stirring, the resulting solution was bubbled with a slow stream of $N_2$ for 30 minutes. Subsequently the reaction mixture was heated to 55° C. and was stirred at this temperature for 6 hr under $N_2$ atmosphere. At the end of this time period, the reaction mixture was allowed to cool. The resulting viscous polymer solution was dialyzed against deionized water using a 3500 molecular weight cut-off dialysis membrane. The dialyzed solution was lyophilized yielding 24.6 g of the polymer as an off white solid.

Preparation 14

Synthesis of epichlorohydrin crosslinked poly[4-{(tris(2-aminoethyl)amino)methyl} styrene] (Compound 15 crosslinked).

A 300 mL beaker was charged with 13 g of poly[4-{tris(2-aminoethyl)amino)methyl} styrene] (preparation 13b) and 70 mL of deionized water. The mixture was stirred until a homogeneous solution of the polymer was obtained. The pH of the polymer solution was brought to 11.0 by slow addition of 50% (w/w) aqueous sodium hydroxide. To the stirred polymer solution was added 0.225 mL of epichlorohydrin and the reaction mixture was allowed to stir until a gel was formed. The stirring was stopped and the gel was left to cure at 30° C. for 18 hr. Subsequently the polymer gel was broken into smaller pieces, dispersed in 2 L of deionized water, stirred for 40 minutes, and filtered. The polymer was filtered, dispersed in 2 L of deionized water and to this dispersion was added 37% HCl solution to bring the pH to 7.7, stirred for 40 minutes, and filtered. Finally, the polymer particles were dispersed in 2 L of deionized water, stirred for 40 minutes, filtered and the filtered polymer was dried at 60° C. yielding 6.5 g of the polymer as an off white solid.

Preparation 15

Synthesis of N,N'-Bis(4-vinylbenzyl)ethylenediamine.

In a 500 mL, 3-necked round-bottomed flask were taken 5.31 grams of 1,2-ethylenediamine and 32.48 g of anhydrous potassium carbonate, and 300 mL of chloroform. To this suspension was added 30 g of 4-vinylbenzyl chloride. The resulting reaction mixture was stirred at 25° C. for 18 hr. Subsequently the reaction mixture was filtered. The solvent was moved under reduced pressure. To the residue was added 300 mL of deionized water followed by 37% aqueous HCl until the pH of the solution was 2.0. The resulting aqueous solution was extracted with tert-butyl methyl ether (2×250 mL). The aqueous layer was collected and was treated with 40% (w/w) NaOH until the pH of the solution was 11.4. The resulting aqueous solution was extracted with tert-butyl methyl ether (2×250 mL). The organic layers were combined and dried over anhydrous sodium sulfate. After filtration, the solvent was removed under reduced pressure yielding 3 g of the product as a light yellow oil.

Preparation 16

Synthesis of Poly [4-{(tris(3-aminopropyl)amino)methyl}styrene] (Compound 16).

The synthesis of this polymer involves two steps: synthesis of the monomer and its subsequent free radical polymerization.

Preparation 16a

Synthesis of [4-{(tris(3-aminopropyl)amino)methyl}styrene].

In a 500 mL, 3-necked round-bottomed flask were taken 102 g of tris(3-aminoethyl)amine and 19.8 g of anhydrous potassium carbonate. To this suspension was added a solution of 18.4 g of 4-vinylbenzyl chloride in 30 mL of chloroform slowly. The resulting reaction mixture was stirred at 25° C. for 18 hr. Subsequently the reaction mixture was filtered. The filtrate was extracted with borate buffer of pH 9.5 (2×400 mL).

Preparation 16b

Polymerization of [4-{(tris(3-aminopropyl)amino)methyl}styrene].

In a 500 mL, 3-necked round-bottomed flask were taken 14 g of {(tris(3-aminopropyl)amino)methyl}styrene (example 4a) and 125 mL of deionized water. To this solution, 37% aqueous HCl was added slowly (by maintaining the temperature to below 15° C. by using an ice-bath) until the pH of the solution reached 1.1. This was followed by the addition of 500 mg of V-50. While stirring resulting solution was bubbled with a slow stream of $N_2$ for 30 minutes. Subsequently the reaction mixture was heated to 55° C. and was stirred at this temperature 12 hr under $N_2$ atmosphere. At the end of this time period, the reaction mixture was allowed to cool. The resulting viscous polymer solution was dialyzed against deionized water using a 3500 molecular weight cut-off dialysis membrane. The dialyzed solution was lyophilized yielding 15.8 g of the polymer as an off white solid.

Preparation 17

Synthesis of epichlorohydrin crosslinked poly[4-{(tris(3-aminopropyl)amino)methyl}styrene] (Compound 16 crosslinked).

In a 300 mL beaker were taken 15 g of poly[4-{tris(3-aminopropyl)amino)methyl}styrene] (preparation 16b) and 60 mL of deionized water. The mixture was stirred until a homogeneous solution of the polymer was obtained. The pH of the polymer solution was brought to 11.0 by slow addition of 50% (w/w) aqueous sodium hydroxide. To the stirred polymer solution was added 0.24 mL of epichlorohydrin and the reaction mixture was allowed to stir until a gel was formed. The stirring was stopped and the gel was left to cure at 30° C. for 18 hr. Subsequently the polymer gel was broken into smaller pieces, dispersed in 2 L of deionized water, stirred for 40 minutes, and filtered. The polymer was filtered, dispersed in 2 L of deionized water and to this dispersion was added 37% HCl solution to bring the pH to 7.8, stirred for 40 minutes, and filtered. Finally, the polymer particles were dispersed in 2 L of deionized water, stirred for 40 minutes, filtered and the filtered polymer was dried at 60° C. yielding 9 g of the polymer as an off white solid.

Preparation 18

Synthesis of Poly [N-{3-[4-vinyl)benzyl aminopropyl}-1.3-diaminopropane](Compound 24).

The synthesis of this polymer involves two steps: synthesis of the monomer and its subsequent free radical polymerization.

Preparation 18a

Synthesis of N-{3-[4-vinyl)benzyl aminopropyl}-1.3-diaminopropane.

In a 2 L, 3-necked round-bottomed flask were taken 167 ml bis(3-aminopropyl)amine, 1370 mL of anhydrous chloroform, and 43.4 g of anhydrous potassium carbonate. To this suspension was added a solution of 37 g of 4-vinylbenzyl chloride in 25 mL of chloroform using an addition funnel. The resulting reaction mixture was stirred at 25° C. of 18 hr and was subsequently filtered. The filtrate was extracted with borate buffer of pH 9.5 (2×1300 mL). The pH of the combined aqueous extract was brought to 12.1 by adding 40% (w/w) aqueous sodium hydroxide solution. The resulting solution was extracted with chloroform (3×1 L). The combined organic phase was dried over anhydrous potassium carbonate, filtered, and the solvent was removed under reduced pressure yielding 42.5 g of the product as a light yellow oil.

Preparation 18b

Polymerization of N-{3-[4-vinyl)benzyl aminopropyl}-1,3-diaminopropane.

In a 250 mL, 3-necked round-bottomed flask were taken 10 g of {3-(4-vinyl)benzyl amino propyl}-1,3 diaminopropane (preparation 18b) and 90 mL of deionized water. To this solution, 37% aqueous HCl was added slowly (by maintaining the temperature below 15° C. by using an ice-bath) until the pH of the solution was 1.2. This was followed by the addition of 100 mg of V-50. While stirring, the resulting solution was bubbled with a slow stream of $N_2$ for 30 minutes. Subsequently the reaction mixture was heated to 55° C. and was stirred at this temperature 6 hr under $N_2$ atmosphere. At the end of this time period, the reaction mixture was allowed to cool. The resulting viscous polymer solution was dialyzed against deionized water using a 3500 molecular weight cut-off dialysis membrane. The dialyzed solution was lyophilized yielding 11.2 g of the polymer as an off white solid.

Preparation 19

Synthesis of epichlorohydrin crosslinked poly[N-{3-(4-vinyl)benzyl aminopropyl}-1,3-diaminopropane](Compound 24 crosslinked).

In a 100 mL beaker were 7 g of poly[N-{3-(4-vinyl)benzyl aminopropyl}-1,3-diaminopropane)] (example 5b) and 26 mL of deionized water. The mixture was stirred until a homogeneous solution of the polymer was obtained. The pH of the polymer solution was brought to 11.0 by slow addition of 50% (w/w) aqueous sodium hydroxide. To the stirred polymer solution was added 0.14 mL of epichlorohydrin and the reaction mixture was allowed to stir until a gel was formed. The stirred was stopped and the gel was left to cure at 30° C. for 18 hr. Subsequently the polymer gel was broken into smaller pieces, dispersed in 1 L of deionized water, stirred for 40 minutes, and filtered. The polymer was filtered, dispersed in 1 L of deionized water and to this dispersion was added 37% HCl solution to bring the pH to 7.7, stirred for 40 minutes, and filtered. Finally, the polymer particles were dispersed in 2 L of deionized water, stirred for 40 minutes, filtered and the filtered polymer was dried at 60° C. yielding 4.3 g of the polymer as an off white solid.

Preparation 20

Synthesis of Poly [4-{(tris(2-aminoethyl)amino) methyl}styrene-co-ethylenebisacrylamide] (Compound 18).

In a 250 mL, 3-necked round-bottomed flask were taken 15.0 g of {(tris(2-aminoethyl) amino)methyl}styrene, 0.5 g N,N-ethylenebisacrylamide, and 35 mL of deionized water. To this solution was added 0.75 g of freshly prepared 20% V-50 in deionized water. While stirring the resulting solution was degassed by bubbling with a slow stream of nitrogen for 30 minutes. Subsequently the reaction mixture was heated to 60° C. and was heated at this temperature for 18 hr under a nitrogen atmosphere, After heating for 30 min at 60° C. a gel formed. Heating was continued without stirring. At the end of this time period, the reaction mixture was allowed to cool. The resulting gel was broken into small pieces and washed with methanol (3×1 L). The polymer gel was then washed with deionized water (2×1 L). the washed swollen polymer gel was stirred in deionized water (1 L) and concentrated HCl was added until pH 7. The slurry was filtered and the swollen polymer was dried in a 60° C. forced-air oven to afford 12.6 g of the polymer.

Preparation 21

Poly [4-{(tris(2-aminoethyl)amino)methyl}styrene-co-ethylenebisacrylamide] (Compound 19).

In a 250 mL, 3-necked round-bottomed flask were taken 15.0 g of {(tris(2-aminoethyl)amino)methyl}styrene, 1.0 g N,N-ethylenebisacrylamide, and 35 mL of deionized water. To this solution was added 0.75 g of freshly prepared 20% V-50 in deionized water. While stirring the resulting solution was degassed by bubbling with a slow stream of nitrogen for 30 minutes. Subsequently the reaction mixture was heated to 60° C. and was heated at this temperature for 18 hr under a nitrogen atmosphere. After heating for 30 min at 60° C. a gel formed. Heating was continued without stirring. At the end of this time period, the reaction mixture was allowed to cool. The resulting gel was broken into small pieces and washed with methanol (3×1 L). The polymer gel was then washed with deionized water (2×1 L). The washed swollen polymer gel was stirred in deionized water (1 L) and concentrated HCl was added until pH 7. The slurry was filtered and the swollen polymer was dried in a 60° C. forced-air oven to afford 14.0 g of the polymer.

Preparation 22

Poly [4-{(tris(2-aminoethyl)amino)methyl}styrene-co-N,N'-bis[(4-vinyl)benzyl)ethylenediamine] (Compound 19).

In a 250 mL, 3-necked round-bottomed flask were taken 15.0 g of {(tris(2-aminoethyl)amino)methyl}styrene, 0.83 g N,N'bis-(4-vinyl)benzyl)ethylenebisamine, and 35 mL of deionized water. To this solution was added 0.75 g of freshly prepared 20% V-50 in deionized water. While stirring the resulting solution was degassed by bubbling with a slow stream of nitrogen for 30 minutes. Subsequently the reaction mixture was heated to 60° C. and was heated at this temperature for 18 hr under a nitrogen atmosphere, After heating for 4 hr at 60° C. a gel formed. Heating was continued without stirring. At the end of this time period, the reaction mixture was allowed to cool. The resulting gel was broken into small pieces and washed with methanol (3×1 L). The polymer gel was then washed with deionized water (2×1 L). The washed swollen polymer gel was stirred in deionized water (1 L) and concentrated HCl was added until pH 7. The slurry was filtered and the swollen polymer was dried in a 60° C. forced-air oven to afford 13.0 g of the polymer.

Preparation 23

Synthesis of Poly[N-{3-(2(bis(2-aminoethyl)amino)ethylamino)propyl}acrylamide] (Compound 21).

The compound 21 was synthesized through six steps as shown in Scheme 1 below. Synthesis of all the intermediates to obtain the desired polymer 21 are described below.

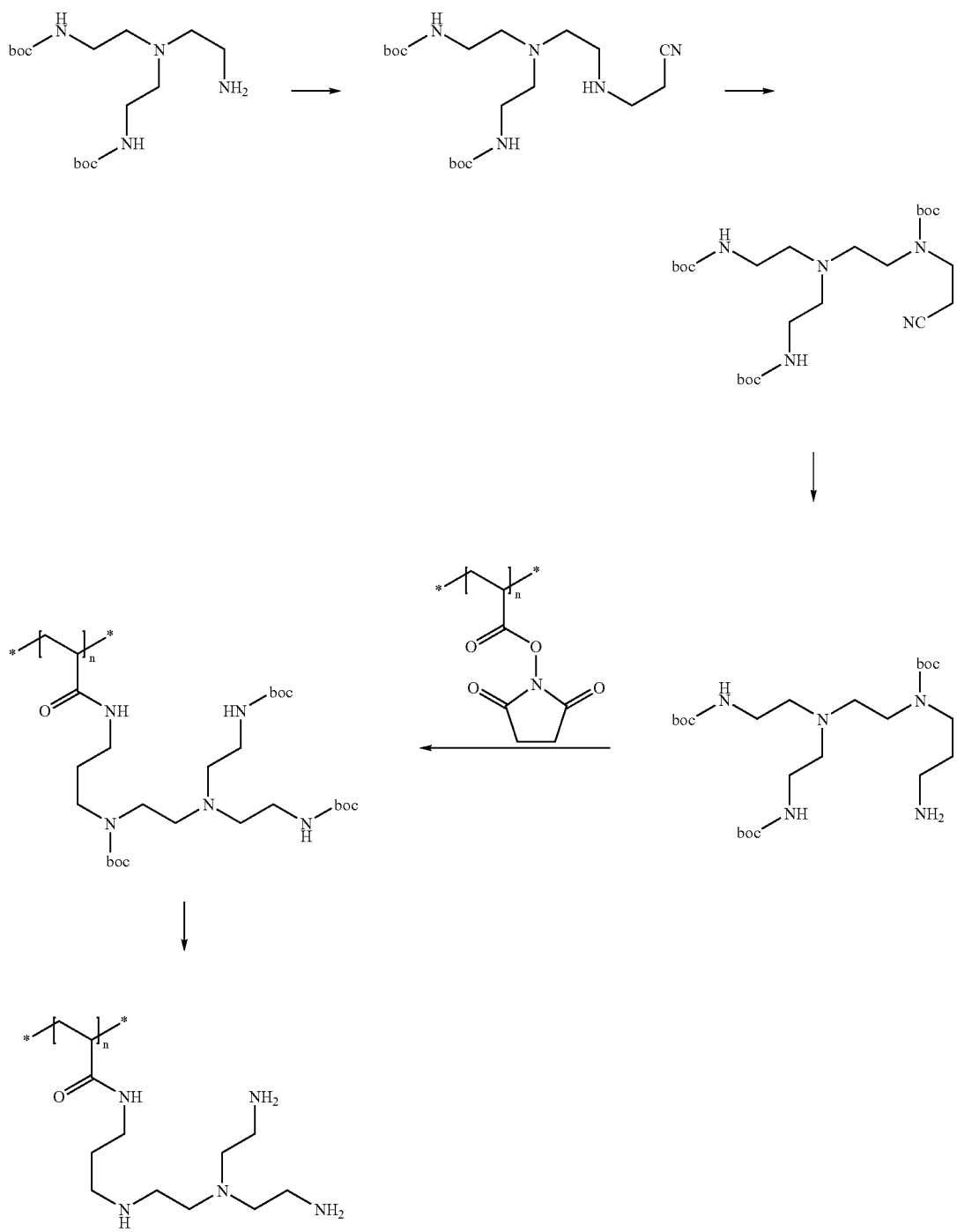

Preparation 23a

Synthesis of 4-(2-Aminoethyl)-1,7-di-(tert-butoxycarbonyl)-1,4,7-triazaheptane (Step 1)

A solution of 102.5 g 2-(tert-butoxycarbonyl-oximino)-2-phenytacetonitrile (0.416 mol) in 300 mL of THF was added to a solution of 30.3 g of tris(2-aminoethyl)amine (0.207 mol) at 0-5 degrees Celsius over a period of 2 h. After stirring the reaction solution at room temperature overnight, the solvent was concentrated on a rotary evaporator. Diethyl ether (600 mL) and 375 mL of water were added and the resulting suspension was adjusted to pH 3.0 by the addition of 25 mL concentrated HCl. The phases were separated and the aqueous phase was washed three times with 600 mL of diethyl ether and all of the ether layers were combined. The combined ether phases were washed twice with 375 mL water. The aqueous layers were combined and the pH of the solution was adjusted to 10 by the addition of 60 mL of 4 N sodium hydroxide solution. The basified aqueous solution was extracted three times with 400 mL of diethyl ether. The ether extracts were combined and washed twice with 160 mL of water and dries over sodium sulfate. The solution was concentrated under reduced pressure on a rotary evaporator afforded 31 g of the crude compound as an oil. Purification with silica gel flash chromatography using methylene chloride and methanol (80:20) as eluent afforded 13 g of the title compound as an oil.

Preparation 23b

Synthesis of di t-boc protected 3-(2(bis(2-aminoethyl)amino)ethyl-amino)propanenitrile (Step 2).

To a solution of 4-(2-aminoethyl)-1,7-di-(tert-butoxycarbonyl)-1,4,7-triazaheptane (12 g) in methanol (400 mL) was added acrylonitrile (2.4 mL). After stirring at room temperature for 18 h, the reaction was concentrated on a rotary evaporator. The crude residue was dissolved in methylene chloride (200 mL) and concentrated on a rotary evaporator. This step was repeated twice more and the resulting oil was dried under vacuum to afford 14 g of the title compound.

Preparation 23c

Synthesis of tri t-boc protected 3-(2(bis(2-aminoethyl)amino)ethyl-amino)propanenitrile (Step 3).

To a solution of nitrile compound (preparation 23b) (13.8 g) in methylene chloride (500 mL) under nitrogen was added di-tert-butyl dicarbonate (8.3 g). After stirring for 3 h the mixture was concentrated on a rotary evaporator.
Purification on an automated flash chromatography silica gel column using methylene chloride and methanol (50:50 then (60:40) as eluent afforded 17 g of the desired product as an oil.

Preparation 23d

Synthesis of tri t-boc protected N'-(2(bis(2-aminoethyl)amino)ethyl)propane-1,3-diamine (Step 4).

A suspension of the protected nitrile (preparation 23c) (4 g) in a solvent mixture containing 140 mL of ethanol and 35 mL of tetrahydrofuran were added 2 N NaOH (18 mL) and Raney-nickel (4 g of 50% (w/w/) in water) and the resulting reaction mixture was stirred under a hydrogen atmosphere for 72 h. The Raney-nickel was removed by centrifugation and decanting the solution away from the precipitated material. The solution was concentrated on a rotary evaporator and diluted with water (250 mL). The solution was then extracted with methylene chloride (1×100 mL then 3×90 mL). the combined extracts were dried over sodium sulfate, filtered, and concentrated on a rotary evaporator to afford 4.4 g of the reduced compound as an oil.

Preparation 23e

Synthesis of tri t-boc protected Poly[N-3-(2-(bis(2-aminoethyl)amino)ethylamino)propyl}acrylamide] (Step 5).

To a solution of 2.3 g of poly(N-acryloxysuccinimide) (prepared by polymerization of N-acryloxysuccinimide) and 8.5 g or tri t-boc protected N'-(2-(bis(2-aminoethyl)amino) ethyl)propane-1,3-diamine product (preparation 23d) in 90 mL of N,N-dimethylformamide was heated at 50° C. for 18 h. After cooling to room temperature the reaction solution was poured slowly into water (1 L) with stirring. The precipitated product was allowed to settle and was isolated by decanting the upper aqueous layer. The upper layer was filtered. The precipitate and filtrate were combined, dissolved in methanol, and concentrated on a rotary evaporator to afford 2.5 g of the desired polymer adduct.

Preparation 23f

Synthesis of Poly[N-{3-(2-(bis(2-aminoethyl)amino) ethylamino)propyl}acrylamide] (Step 6).

To a solution of 2.5 g of tri t-boc protected Poly[N-{3-(2-(bis(2-aminoethyl)amino)ethylamino)propyl}acrylamide] (preparation 23 e) in 50 mL of methanol was added 5 mL of concentrated HCl. After stirring 3 h at 35 degrees Celcius the solution was stirred at room temperature for 18 h. A sticky solid had formed in the solution. The methanol layer was poured off from the sticky solid. The sticky solid was dissolved in water (20 mL) and dialyzed (MWCO=3500) against deionized water. Lyophilization afforded 1.5 g of compound 21 as an off white solid.

Preparation 24

Synthesis of Poly $\{N^1,N^1$-diallyl-$N^2$ $N^2$-bis(2-aminoethyl)ethane-1,2-diamine$\}$ (Compound 22).

This polymer was synthesized in two steps; synthesis of the diallyl monomer followed by its polymerization.
Preparation 24a

Synthesis of Poly $N^1,N^1$-diallyl-$N^2$ $N^2$-bis(2-aminoethyl)ethane-1,2-diamine.

To a mixture of 4-(2-Aminoethyl)-1,7-di-(tert-butoxycarbonyl)-1,4,7-triazaheptane (1.5 g), potassium carbonate (2.97 g), and tetrahydrofuran (20 mL) was added allylbromide (1.15 g). After stirring overnight at room temperature, the mixture was filtered and concentrated on a rotary evaporator. Purification on an automated flash chromatography silica gel column using hexane and ethyl acetate (100:0 to 30:70) as eluent afforded a mixture of monoalkylated product and dialkylated product. The material was further purified by stirring with an excess of polystyrene-benzaldehyde resin in tetrahydrofuran overnight at room temperature, filtering, and drying under vacuum to afford 0.9 g of the desired product as an oil.

To 0.5 g of this oil was added 5 mL of tetrahydrofuran and the resulting solution was cooled to 0° C. in an ice water bath. To the cooled solution was added 4 N HCl (0.02 mL). The solution was allowed to slowly warm to room temperature and stirred 18 h. An additional portion of 4 n HCl (0.1 mL) was added and the reaction was allowed to stir another 18 h. Filtration and drying under vacuum over $P_2O_5$ afforded the desired product as a white solid in quantitative yield.

Preparation 24

Synthesis of Poly ($N^1,N^1$-diallyl-$N^2N^2$-bis(2-aminoethyl)ethane-1.2-diamine.

A solution containing 0.6 g of $N^1,N^1$-diallyl-$N^2N^2$-bis(2-aminoethyl)ethane-1,2-diamine.2HCl (preparation 24a) and 2,2'-azobis(2-amidinopropane) dihydrochloride (0.006 g) in 1 mL deionized water was degassed with a stream of nitrogen gas for 30 minutes. The solution was heated for 72 h at 60 degrees Celsius. After 24 h of heating another portion of 2,2'-azobis(2-amidinopropane) dihydrochloride (0.006 g) was added, After 48 h of heating a third portion of 2,2'-azobis (2-amidinopropane) dihydrochloride (0.006 g) was added. After cooling to room temperature the reaction mixture was dialyzed (membrane MW cut-off 3.5K) against deionized water. Lyophilization afforded the desired product 22 as an off white solid.

Some crosslinking monomers shown below are used to prepare polymer gels by crosslinking copolymerization. Their synthesis is exemplified in the example shown above (Preparation 15).

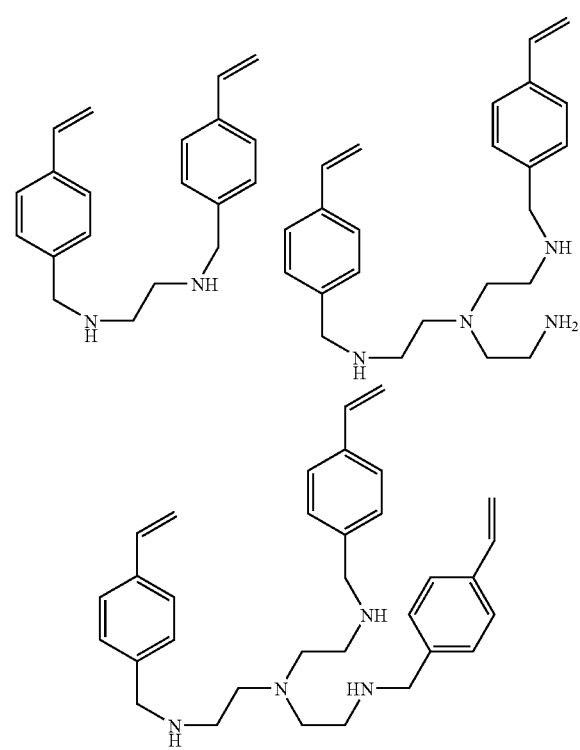

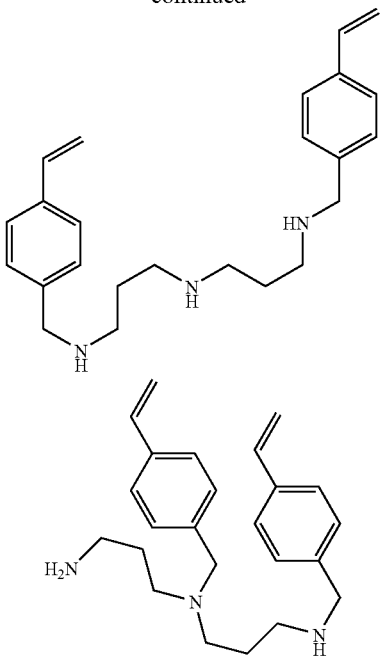

In Vitro Phosphate Binding

In vitro phosphate binding properties of polymeric hydrogels bearing phosphate receptors (Compounds 9, 10, and 11) were determined by Langmuir isotherm measurements. The binding isotherm curves were constructed from solutions containing initial concentrations of 1.0, 2.5, 7.5, 14.5, and 30.0 mM of $KH_2PO_4$ in 80 mM NaCl and 100 mM N,N-bis (hydroxyethyl)-2-aminoethanesulfonic acid at pH 7.

For each initial phosphate solution concentration, 53.5 mg (dry weight) of the polymer was used and the experiments were run in duplicate. Thus, 20 mL of the appropriate solution was added to the polymer sample taken in a 50 mL centrifuge tube. Each solution was then placed in an orbital shaker (maintained at 37° C.) at 360 revolutions per minute for 3 hours. Subsequently, the polymer gel was separated from the solution by filtration using a polyether sulfone membrane filter of pore size 0.8/0.2 μM. The concentration of phosphate remaining in the solution after filtration from the insoluble sample was determined by inductively coupled plasma-optical emission spectroscopy. The emission line at 213.618 nm for phosphate was used. The amounts of phosphate found in the filtrate for various initial concentrations were used to estimate the phosphate binding properties of these polymers. The results are summarized in Table 1.

TABLE 1

Results of In Vitro Phosphate Binding Characteristics of Polymeric Hydrogels bearing Phosphate Receptor Groups

| Polymer Tested | Phosphate Binding Capacity (mmol/g of polymer) |
|---|---|
| Compound 9 crosslinked with epichlorohydrin | 5.0 |
| Compound 10 crosslinked with epichlorohydrin | 4.5 |
| Compound 11 crosslinked with epichlorohydrin | 3.4 |

In Vivo Phosphate Binding

House male SD rats singly in wire-bottom cases were given Purina 5002 diet. The animals were allowed at least 5 days to acclimate prior to experimental use. After the end of this time period, these rats were placed in metabolic cages for 48 hours to establish baseline phosphorus excretion. After collecting the urine, the rats were returned to home cages. The phosphorus contents of urine were analyzed with Hitachi analyzer to determine excretion in mg/day. Any rat with outlying values was excluded and the remaining animal were distributed into closely matched groups. Individual polymer samples (Compounds 9, 10, 12, 13, and 14) were mixed with the Purina 5002 certified diet at a concentration of 0.5% (w/w). For each rat in a given group, 200 g of diet was prepared. The body weights of the rats were taken and they were placed on test diets. After 4 days on this diet, the rats were transferred to metabolic cages and given treatment diets. The urine samples were collected at 24 hours (+/−30 minutes) intervals on days 5 and 6 and the phosphorus contents of urine were analyzed with Hitachi analyzer to determine excretion mg/day. The weights rats were taken and used to calculate weight loss or gain and the weights of the remaining diets were taken to calculate food consumer per day. The changes in phosphorus excretion relative to baseline and cellulose negative control were determined to evaluate the phosphate binding properties of these polymers. Lower the percentage of urinary phosphate, better is the phosphate binding property of the hydrogel. The results are summarized in Table 2.

TABLE 2

Results of In Vivo Phosphate Binding Characteristics of Polymeric Hydrogels bearing Phosphate Receptor Groups

| Treatment Agent | Description | Urinary Phosphate % of Control |
|---|---|---|
| Cellulose | Negative Control | 100 |
| Compound 9 crosslinked with epichlorohydrin | Test Compound | 55.4 |
| Compound 10 crosslinked with epichlorohydrin | Test Compound | 67.4 |
| Compound 12 crosslinked with epichlorohydrin | Test Compound | 73 |
| Compound 13 crosslinked with epichlorohydrin | Test Compound | 50 |
| Compound 14 crosslinked with epichlorohydrin | Test Compound | 61 |
| Compound 15 crosslinked with epichlorohydrin | Test Compound | 61 |
| Compound 16 crosslinked with epichlorohydrin | Test Compound | 42 |
| Compound 17 crosslinked with epichlorohydrin | Test Compound | 66 |
| Compound 18 crosslinked with epichlorohydrin | Test Compound | 63 |
| Compound 19 crosslinked with epichlorohydrin | Test Compound | 61 |
| Compound 20 crosslinked with epichlorohydrin | Test Compound | 57 |

What is claimed is:

1. A polymer comprising pendent groups extending from a backbone, each pendent group comprising at least three nitrogen bearing functional groups, at least two of the nitrogen bearing functional groups which bind phosphate, wherein each pendent group is represented by Structural Formula (I):

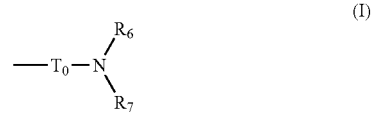

wherein:
each amine in Structural Formula (I) is independently optionally quaternarized with R;
each R is independently hydrogen or an optionally substituted alkyl group;
$T_0$ is a covalent bond, carbonyl, —Ar—, -$T_1$-, —Ar-$T_1$-, —O-$T_2$-, —S-$T_2$-, —C(O)-$T_1$-, —C(O)O-$T_2$-, —C(O)S-$T_1$-, or —C(O)N($R_7$)-$T_2$-, wherein $R_7$ is hydrogen or an optionally substituted C1-C3 alkyl group;
Ar is an optionally substituted arylene group;
$T_1$ is an optionally substituted C1-5 alkylene group optionally interrupted by an optionally substituted arylene group;
$T_2$ is an optionally substituted C2-5 alkylene group; and
a) $NR_6R_7$ taken together is
 1) a monocycle non-aromatic ring substituted with two or more groups selected from amine, ammonium, amino alkyl, and ammonium alkyl,
 or
 2) a bridge bicycle non-aromatic ring comprising at least two ring amine or ammonium groups; or
b) $R_6$ is hydrogen, an optionally substituted alkyl group, or an optionally substituted aryl group, and
 $R_7$ is
 1) represented by Structural Formula (Ia)

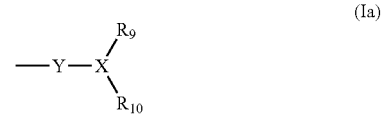

if $T_0$ is O -$T_2$, S-$T_2$, Ar, or Ar-$T_1$;
and
represented by Structural Formula (Ib)

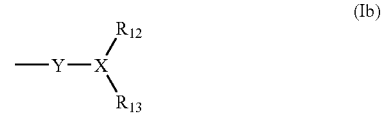

if $T_0$ is a covalent bond, carbonyl, -$T_1$-, —C(O)-$T_1$, C(O)O-$T_2$-, —C(O)S-$T_1$, or —C(O)N($R_7$)-$T_2$-;
where
X is
(A) C-Rx, where Rx is hydrogen, an optionally substituted alkyl group, or an optionally substituted aryl group, or
(B) N or $N_+(R)$,
Y is
(A) a covalent bond or an optionally substituted C1-C10 alkylene group optionally interrupted by an optionally substituted arylene group, if X is C—$R_x$, and
(B) an optionally substituted C2-C10 alkylene group optionally interrupted by an optionally substituted arylene group, if X is N or $N^+(R)$, $R_9$ is
(A) an alkyl group or an aryl group, the group substituted with at least one group selected from amine, ammonium, amino alkyl, and ammonium alkyl, if X is C—$R_x$, and
(B) hydrogen, an optionally substituted alkyl group, or an optionally substituted aryl group, if X is N or W(R),
$R_{10}$ is hydrogen, an optionally substituted alkyl group, or an optionally substituted aryl group, and
$R_{12}$ and $R_{13}$ are each independently an alkyl group terminally substituted with amine or ammonium, or
2) -$Y_1$-Cy,
where $Y_1$ is a covalent bond or an optionally substituted C1-C5 alkylene group, and Cy is a monocyclic non-aromatic ring substituted with two or more groups selected from amine, ammonium, amino alkyl, and ammonium alkyl,
wherein the polymer is not one of
poly(tris(2-aminoethyl)amine-acrylamide) and
polyepichlorohydrin/tris(2-aminoethyl)amine,
wherein the polymer comprises no nitrogen in the polymer backbone, and wherein the polymer comprises no vicinal diamine, vicinal diammonium, vicinal diaminoalkyl or vicinal diammoniumalkyl groups in the polymer backbone; provided that if the polymer comprises a repeat unit represented by any one of Structural Formulas (A)-(G):

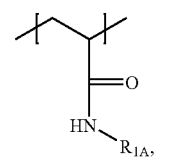
(A)

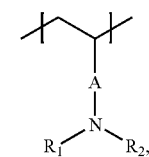
(B)

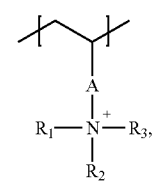
(C)

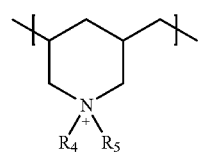
(D)

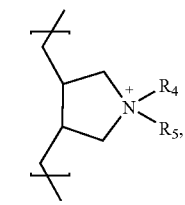
(E)

-continued

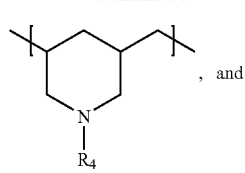
, and
(F)

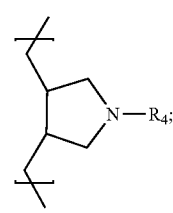
(G)

wherein
A is either a covalent bond, C(O), or $CH_2$;
$R_1$ is an alkyl amine or alkyl ammonium group;
$R_{14}$ is a polyleneimine;
$R_2$ and $R_3$ are each independently hydrogen, an alkyl group, an alkyl amino group, or an aryl group;
$R_4$ is an alkyl ammonium group; and
$R_5$ is hydrogen, or an optionally substituted alkyl group, or an optionally substituted aryl group;
then the polymer comprises a second repeat unit with a multifunctional phosphate binding pendent group, wherein said second repeat unit is not represented by Structural Formulas (A)-(G).

2. The polymer of claim 1, wherein each pendent group is represented by Structural Formula (IIa) or (IIb):

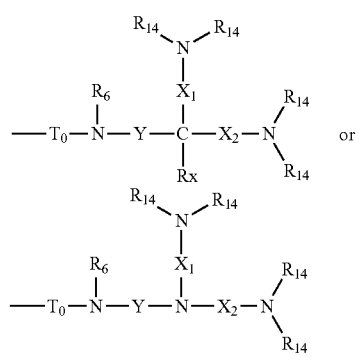
(IIa)

wherein
each amine of Structural Formulas (IIa) and (IIb) is independently optionally quaternarized with R;
each R is independently hydrogen or an optionally substituted alkyl group;
each $R_{14}$ is independently hydrogen or an optionally substituted alkyl group;
and
$X_1$ and $X_2$ are each independently an optionally substituted alkylene group.

3. The polymer of claim 2, wherein:
Y in Structural Formula (IIa) is a C1-5 alkylene group, and Y in Structural Formula (IIb) is a C2-C5 alkylene group; and
$X_1$ and $X_2$ in Structural Formula (IIa) are independently C1-C5 alkylene, and $X_1$ and $X_2$ in Structural Formula (IIb) are independently C2-C05 alkylene;
$R_x$ is hydrogen; and
each $R_{14}$ is hydrogen.

4. The polymer of claim 2, where in the polymer comprises a repeat unit represented by a structural formula selected from:

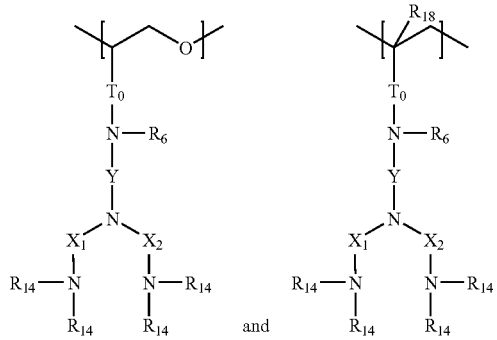

wherein each amine is independently optionally quaternarized with R;

each R is independently hydrogen or an optionally substituted alkyl group; and $R_{18}$ is hydrogen or a C1-C5 alkyl group.

5. The polymer of claim 4, where in the polymer comprises a repeat unit represented by a structural formula selected from:

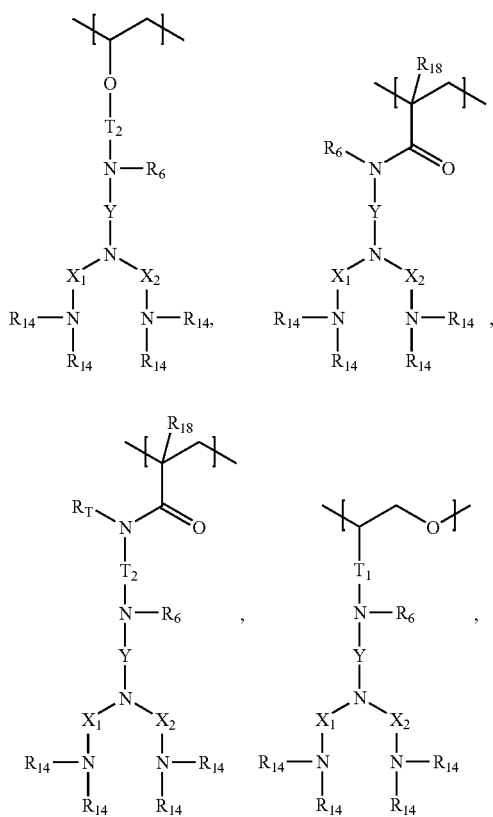

-continued

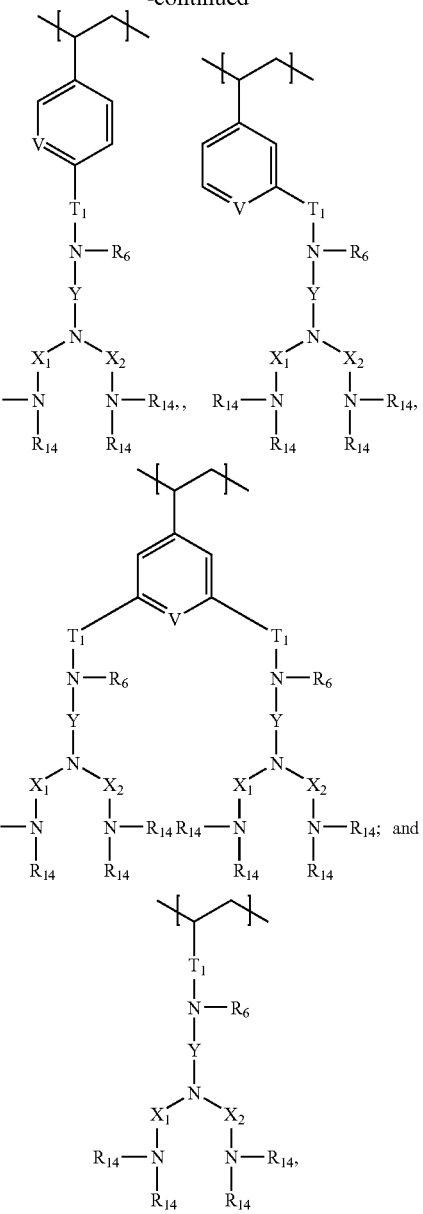

wherein each amine is independently optionally quaternarized with R; and
each V is N or CH;
each R is independently hydrogen or an optionally substituted alkyl group.

6. The polymer of claim 2, wherein the polymer comprises a repeat unit represented by a structural formula selected from:

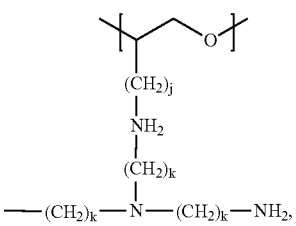

-continued

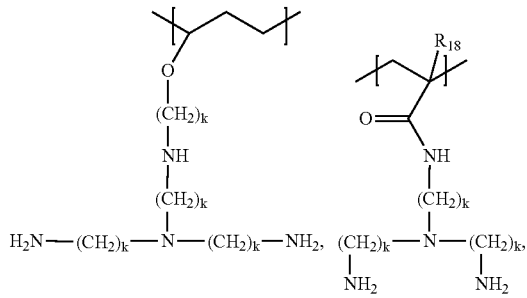

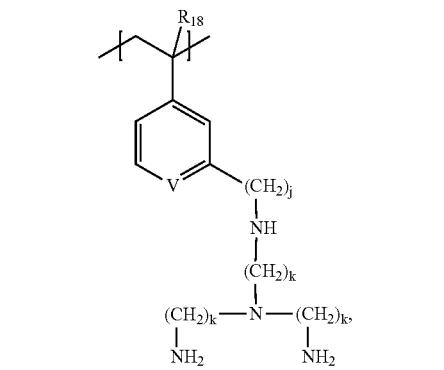

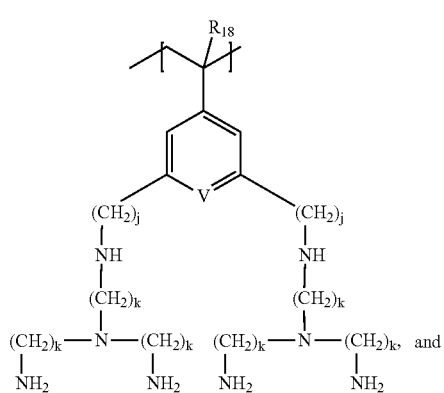

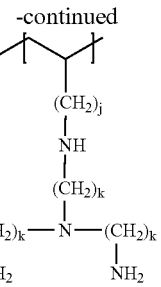

-continued

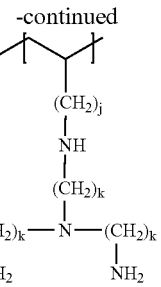

wherein:

R$_{18}$ is hydrogen or a methyl group;

Each V is N or CH;

each amine is independently optionally quaternarized with hydrogen; and each j is independently 1, 2, 3, 4, or 5; and each k is independently 2, 3, or 4.

7. The polymer of claim 1, wherein each pendent group is represented by Structural Formula (III):

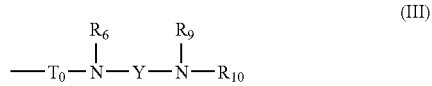

wherein:

each amine in Structural Formula (III) is independently optionally quaternized with R;

each R is independently hydrogen or an optionally substituted alkyl group;

T$_0$ is O-T$_2$, S-T$_2$, Ar, or Ar-T$_1$;

R$_{10}$ is hydrogen, or X$_3$-N(R$_{14}$)$_2$ or $_{X3}$-N$^+$(R$_{14}$)$_3$ with X$_3$ being an option substituted C2-C5 alkylene group; and each R$_{14}$ is independently hydrogen or an optionally substituted alkyl group.

8. The polymer of claim 7, wherein each pendent group is represented by Structural Formula (IV):

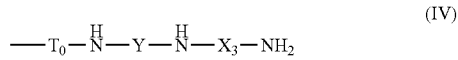

wherein:

each amine shown in Structural Formula (IV) is optionally quaternarized with R;

each R is independently hydrogen or an optionally substituted alkyl group;

and

Y and X$_3$ are independently —(CH$_2$)$_j$— where j is 2, 3, or 4.

9. The polymer of claim 8, wherein the polymer comprises a repeat unit represented by a structural formula selected from:

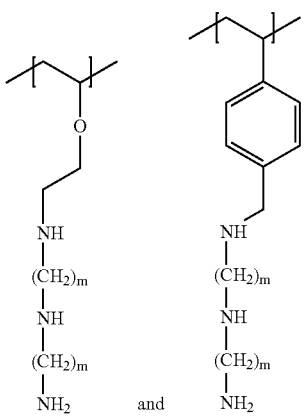

wherein each amine in the structural formulas is independently optionally quaternarized with hydrogen, k is 1, 2, 3, 4, or 5, and each m is independently 2 or 3.

10. The polymer of claim 1, wherein each pendent group is represented by Structural Formula (X):

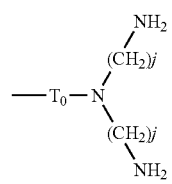

wherein:
T$_0$ is O-T$_2$, S-T$_2$, Ar, or Ar-T$_1$;
each amine in Structural Formula (X) is independently optionally quaternarized with R;
each R is independently hydrogen or an optionally substituted alkyl group;
and
each j is independently 2 or 3.

11. The polymer of claim 10, wherein the polymer comprises a repeat unit given by at least one of the following structural formulas:

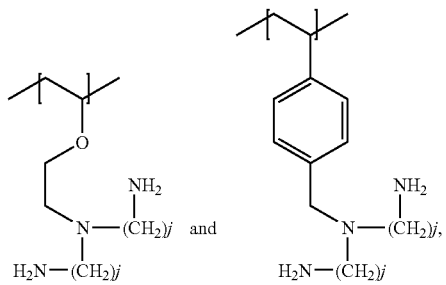

wherein:
each amine in the structural formulas is independently optionally quaternarized with hydrogen; and
each j is independently 2 or 3.

12. The polymer of claim 1, wherein each pendent group is represented by Structural Formula (V):

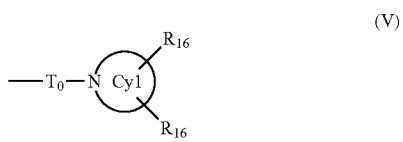

wherein:
each amine in Structural Formula (V) is independently optionally quaternarized with R;
Cy1 is a nitrogen-containing non-aromatic ring with 3 to 7 carbon atoms;
each R is independently hydrogen or an optionally substituted alkyl group;
and
each R$_{16}$ is independently a C1-C3 alkyl chain terminally substituted with amine or ammonium.

13. The polymer of claim 12, wherein the polymer comprises a repeat unit represented by at least one of the following structural formulas:

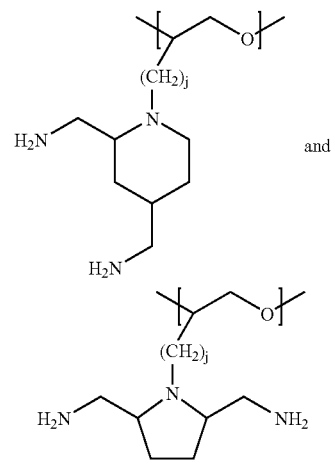

wherein each amine is independently optionally quaternarized with hydrogen and j is 1, 2, 3, or 4.

14. The polymer of claim 1, wherein each pendent group is represented by Structural Formula (VI):

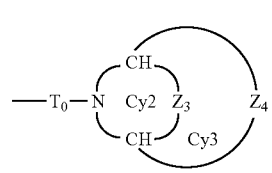

wherein:
each amine in Structural Formula (VI) is independently optionally quaternarized with R;
each R is independently hydrogen or an optionally substituted alkyl group;
Z$_3$ and Z$_4$ are each independently amine or ammonium; and
Cy2 and Cy3 are each independently a 5, 6, or 7 member, non-aromatic ring with two ring nitrogen atoms.

15. The polymer of claim 14, where in each pendent group is represented by the following structural formula:

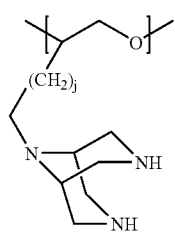

wherein each amine in the structural formula is independently optionally quaternarized with hydrogen and j is 1, 2, 3, or 4.

16. The polymer of claim 1, where in each pendent group is represented by Structural Formula (IX):

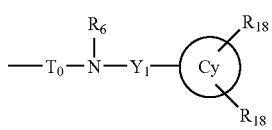

(IX)

wherein:
- each amine in Structural Formula (IX) is independently optionally quaternarized with R;
- Cy is a non-aromatic ring with 3 to 7 carbon atoms;
- each R is independently hydrogen or an optionally substituted alkyl group; and
- each $R_{18}$ is independently a C1-C3 alkyl chain terminally substituted with amine or ammonium.

17. The polymer of claim 16, wherein the polymer comprises a repeat unit represented by at least one of the following structural formulas:

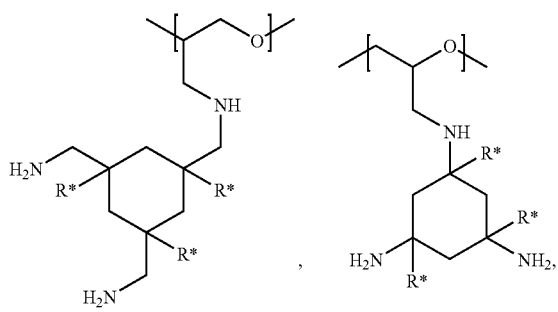

wherein:
- each amine in the structural formula is independently optionally quaternarized with R; and
- each R and each R* is independently C1-C3 alkyl or hydrogen.

18. A polymer comprising a repeat unit represented by one of Structural Formulas (VII) and (VIII):

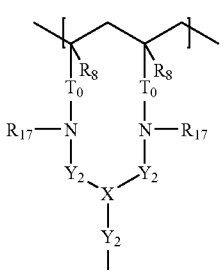

(VII)

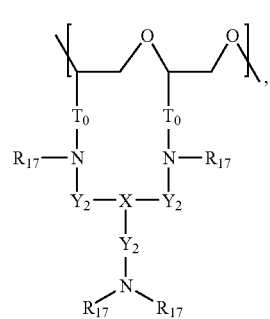

(VIII)

wherein:
- each amine in Structural Formulas (VII) and (VIII) is independently optionally quaternarized with R;
- each R is independently hydrogen or an optionally substituted alkyl group;
- $R_8$ Is hydrogen or methyl;
- each $R_{17}$ is independently hydrogen or an optionally substituted C1-C5 alkyl;
- Ar is an optionally substituted arylene group;
- each $T_o$ is independently a covalent bond, carbonyl, —Ar—, —Ar-$T_1$-, -$T_1$-, —O-$T_2$-, —S-$T_2$-, —C(O)-$T_1$-, —C(O)O-$T_2$-, —C(O)S-$T_1$-, or —C(O)N($R_7$)-$T_2$-,
    wherein $R_7$ is hydrogen or an optionally substituted C1-C3 alkyl group;
- $T_1$ is an optionally substituted C1-C5 alkylene group optionally interrupted by an optionally substituted arylene group;
- $T_2$ is an optionally substituted C2-C5 alkylene group;
- X is C-$R_x$, N, or $N^+$ (R), where $R_x$ is hydrogen or an optionally substituted alkyl group; and
- each $Y_2$ is independently
  (i) optionally substituted C2-5S alkylene when X is N or $N^+$(R), and
  (ii) optionally substituted C1-C5 alkylene when X is C-Rx.

* * * * *

UNITED STATES PATENT AND TRADEMARK OFFICE
CERTIFICATE OF CORRECTION

PATENT NO. : 8,986,669 B2
APPLICATION NO. : 11/991209
DATED : March 24, 2015
INVENTOR(S) : Chad C. Huval et al.

It is certified that error appears in the above-identified patent and that said Letters Patent is hereby corrected as shown below:

On the title page, in column 2, item 56 under "Other Publications", line 2, delete "(propul" and insert -- (propyl --, therefor.

On the page 3, in column 2, item 56 under "Other Publications", line 2, delete "Analgous" and insert -- Analogous --, therefor.

On the page 3, in column 2, item 56 under "Other Publications", line 22, delete "(sulfonamine)s" and insert -- (sulfon-amine)s --, therefor.

On the page 3, in column 2, item 56 under "Other Publications", line 55, delete "Crosslnker" and insert -- Crosslinker --, therefor.

On the page 3, in column 2, item 56 under "Other Publications", lines 60-61, delete "propylenimin)-Dendrimere:" and insert -- propylenimine)-Dendrimer: --, therefor.

On the page 4, in column 2, item 56 under "Other Publications", line 23, delete "Distintegration" and insert -- Disintegration --, therefor.

In the specification

In column 3, line 27, delete "allyl" and insert -- alkyl --, therefor.

In column 4, line 21, delete "allyl" and insert -- alkyl --, therefor.

In column 5, line 30, delete "allyl" and insert -- alkyl --, therefor.

In column 5, line 56, delete "allyl" and insert -- alkyl --, therefor.

In column 6, line 1, delete "C1-C 10" and insert -- C1-C10 --, therefor.

In column 6, line 14, delete "allylene" and insert -- alkylene --, therefor.

In column 7, line 11, delete "allylene" and insert -- alkylene --, therefor.

In column 7, line 27, delete "allylene" and insert -- alkylene --, therefor.

In column 10, line 36, delete "IIm)" and insert -- (IIm) --, therefor.

In column 12, line 24, delete "substitutent" and insert -- substituent --, therefor.

Signed and Sealed this
Eighth Day of March, 2016

Michelle K. Lee
*Director of the United States Patent and Trademark Office*

CERTIFICATE OF CORRECTION (continued)
U.S. Pat. No. 8,986,669 B2

In the specification

In column 12, line 25, delete "indepentyl" and insert -- independently --, therefor.

In column 12, line 53, delete "allyl" and insert -- alkyl --, therefor.

In column 13, line 2, delete "allyl" and insert -- alkyl --, therefor.

In column 13, line 43, delete "allyl" and insert -- alkyl --, therefor.

In column 17, line 9, delete "quarternized" and insert -- quaternized --, therefor.

In column 17, line 33, delete "($T_o$" and insert -- ($T_0$ --, therefor.

In column 17, line 33, delete "($T_o$" and insert -- ($T_0$ --, therefor.

In column 17, line 34, delete "($T_o$" and insert -- ($T_0$ --, therefor.

In column 18, line 45, delete "$T_o$" and insert -- $T_0$ --, therefor.

In column 18, line 64, delete "quarternized" and insert -- quaternized --, therefor.

In column 18, line 64, delete "allyl" and insert -- alkyl --, therefor.

In column 20, line 36, delete "diaimine" and insert -- diamine --, therefor.

In column 20, line 44, delete "lammoniumalkyl" and insert -- ammoniumalkyl --, therefor.

In column 21, line 13, delete "orpolyacrylates." and insert -- or polyacrylates. --, therefor.

In column 22, line 30, delete "allyle," and insert -- allyl, --, therefor.

In column 23, line 5, delete "butylvinyltether," and insert -- butylvinylether, --, therefor.

In column 23, line 22, delete "crosslinring" and insert -- crosslinking --, therefor.

In column 23, line 32, delete "toluence" and insert -- toluene --, therefor.

In column 25, line 9, delete "allylene" and insert -- alkylene --, therefor.

In column 25, line 36, delete "allylene" and insert -- alkylene --, therefor.

In column 25, line 62, delete "allyl" and insert -- alkyl --, therefor.

In column 27, line 8, delete "tablets" and insert -- tablets. --, therefor.

In column 27, line 52, delete "shell" and insert -- shell. --, therefor.

In column 34, line 18, delete "aminoethy)" and insert -- aminoethyl) --, therefor.

In column 34, line 22, delete "3pyrrolidinone" and insert -- 3-pyrrolidinone --, therefor.

In column 35, line 18, delete "pyrrolidione" and insert -- pyrrolidinone --, therefor.

In column 35, line 31, delete "Epichlorhydrin" and insert -- Epichlorohydrin --, therefor.

In column 37, line 58, delete "this," and insert -- this --, therefor.

In column 37, lines 61-62, delete "diethyl ether," and insert -- diethylether, --, therefor.

In column 38, lines 47-48, delete "0.1 L" and insert -- 1 L --, therefor.

In column 41, line 13, delete "-1.3-" and insert -- -1,3- --, therefor.

In column 41, line 21, delete "-1.3-" and insert -- -1,3- --, therefor.

In column 42, line 27, delete "atmosphere," and insert -- atmosphere. --, therefor.

In column 43, line 7, delete "atmosphere," and insert -- atmosphere. --, therefor.

In the specification

In column 45, line 7, delete "phenytacetonitrile" and insert -- phenylacetonitrile --, therefor.

In column 46, line 5, delete "the" and insert -- The --, therefor.

In column 46, line 38, delete "Celcius" and insert -- Celsius --, therefor.

In column 46, line 48, delete "$N^2\ N^2$" and insert -- $N^2,N^2$ --, therefor.

In column 46, line 55, delete "$N^2\ N^2$" and insert -- $N^2,N^2$ --, therefor.

In column 47, line 14, delete "Preparation 24" and insert -- Preparation 24b --, therefor.

In column 47, line 16, delete "$N^2N^2$" and insert -- $N^2,N^2$ --, therefor.

In column 47, line 17, delete "1.2-" and insert -- 1,2- --, therefor.

In column 47, line 20, delete "$N^2N^2$" and insert -- $N^2,N^2$ --, therefor.

In column 47, line 27, delete "added," and insert -- added. --, therefor.

In the claims

In column 50, line 13, in claim 1, delete "-$T_1$-, —Ar-$T_1$-," and insert -- —Ar—$T_1$—, —$T_1$—, --, therefor.

In column 50, line 18, in claim 1, delete "C1-5" and insert -- C1-C5 --, therefor.

In column 50, line 21, in claim 1, delete "C2-5" and insert -- C2-C5 --, therefor.

In column 50, line 56, in claim 1, delete "Rx," and insert -- $R_x$, --, therefor.

In column 50, line 56, in claim 1, delete "Rx" and insert -- $R_x$ --, therefor.

In column 52, line 21, in claim 1, delete "polyleneimine;" and insert -- polyalkyleneimine; --, therefor.

In column 52, lines 42-47, in claim 2, delete " 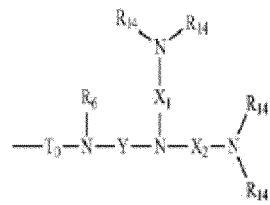 " and insert

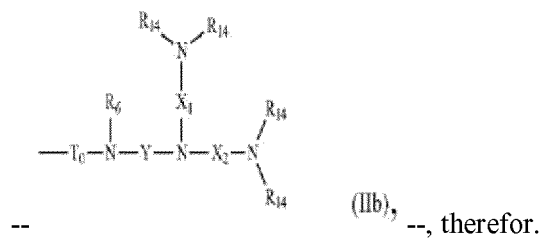

-- --, therefor.

In column 52, line 60, in claim 3, delete "C1-5" and insert -- C1-C5 --, therefor.

In column 52, line 65, in claim 3, delete "C2-C05" and insert -- C2-C5 --, therefor.

In column 53, line 1, in claim 4, delete "where in" and insert -- wherein --, therefor.

In column 53, line 31, in claim 5, delete "where in" and insert -- wherein --, therefor.

CERTIFICATE OF CORRECTION (continued)
U.S. Pat. No. 8,986,669 B2

In the claims

In column 53, lines 51-66, in claim 5, delete " 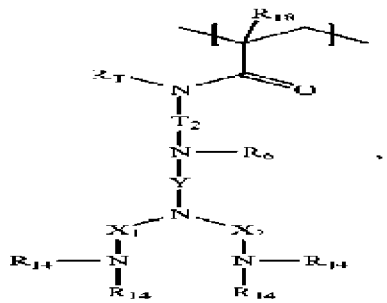 " and insert -- 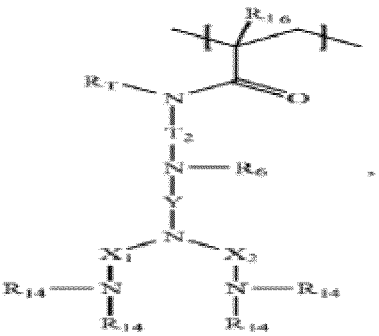 --, therefor.

In column 54, lines 1-9, in claim 5, delete " 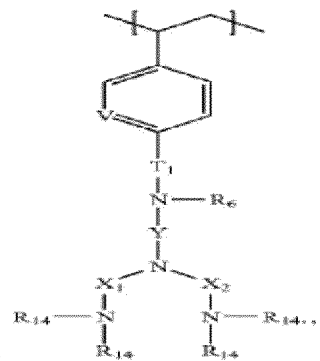 " and insert -- 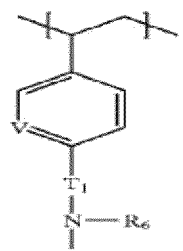 --, therefor.

In the claims

In column 55, lines 16-32, in claim 6, delete " 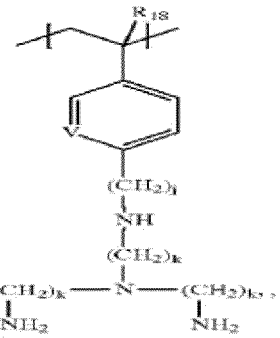 " and insert -- 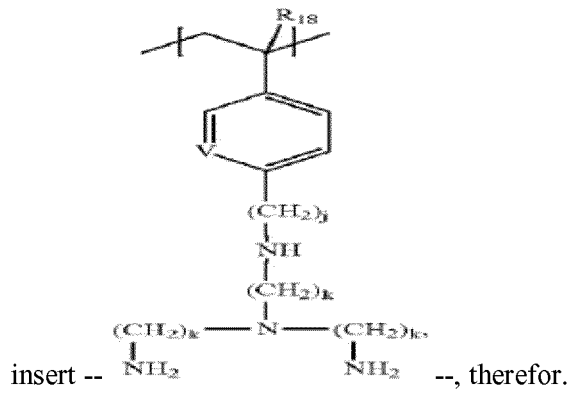 --, therefor.

In column 56, line 40, in claim 7, delete "$x_3$-" and insert -- $X_3$- --, therefor.

In column 56, line 41, in claim 7, delete "option" and insert -- optionally --, therefor.

In column 58, line 66, in claim 15, delete "where in" and insert -- wherein --, therefor.

In column 59, line 15, in claim 16, delete "where in" and insert -- wherein --, therefor.

In column 60, line 35, in claim 18, delete "Is" and insert -- is --, therefor.

In column 60, line 37, in claim 18, delete "alkyl;" and insert -- alkyl group; --, therefor.

In column 60, line 39, in claim 18, delete "$T_o$" and insert -- $T_0$ --, therefor.

In column 60, line 52, in claim 18, delete "C2-5S" and insert -- C2-C5 --, therefor.

In column 60, line 56, in claim 18, delete "Rx." and insert -- $R_x$. --, therefor.